(12) United States Patent
Ebron et al.

(10) Patent No.: US 7,842,637 B2
(45) Date of Patent: Nov. 30, 2010

(54) ELECTROACTIVATED FILM WITH POLYMER GEL ELECTROLYTE

(75) Inventors: Von Howard M. Ebron, Springfield, MO (US); Yevgenia V. Ulyanova, Meridianville, AL (US); Shifeng Hou, Pine Brook, NJ (US); Sriram Viswanathan, Springfield, MO (US); Patrick J. Kinlen, Fenton, MO (US)

(73) Assignee: Lumimove, Inc., St. Louis, MO (US)

( * ) Notice: Subject to any disclaimer, the term of this patent is extended or adjusted under 35 U.S.C. 154(b) by 0 days.

(21) Appl. No.: 12/215,348

(22) Filed: Jun. 26, 2008

(65) Prior Publication Data

US 2009/0291843 A1 Nov. 26, 2009

Related U.S. Application Data

(60) Provisional application No. 61/128,953, filed on May 23, 2008.

(51) Int. Cl.
*C08F 4/02* (2006.01)
*A61L 2/08* (2006.01)
*C12M 1/00* (2006.01)

(52) U.S. Cl. .................... 502/160; 422/28; 204/403.06
(58) Field of Classification Search ........................ None
See application file for complete search history.

(56) References Cited

U.S. PATENT DOCUMENTS

| | | | |
|---|---|---|---|
| 4,774,285 A | 9/1988 | Pfohl et al. .................... 525/60 |
| 5,227,042 A | 7/1993 | Zawodzinski et al. | |
| 5,326,809 A | 7/1994 | Bott et al. .................... 524/459 |
| 5,518,624 A | 5/1996 | Filson et al. | |
| 5,847,120 A | 12/1998 | Collins et al. ................ 540/460 |
| 6,011,152 A | 1/2000 | Gordon-Wylie et al. ..... 540/474 |
| 6,051,704 A | 4/2000 | Gordon-Wylie et al. ..... 540/465 |
| 6,054,580 A | 4/2000 | Collins et al. ................ 540/460 |
| 6,056,796 A | 5/2000 | Chiang et al. | |

(Continued)

FOREIGN PATENT DOCUMENTS

EP  0 339 371 A2  4/1989

(Continued)

OTHER PUBLICATIONS

Chagnes et al. "Thermal analysis of gamm butyrolactone and 1 butyl 3 methyl imidazolium ionic liquids mixtures" Solid State Ionics 176 (2005) 1419-1427.*

(Continued)

*Primary Examiner*—Melvin C Mayes
*Assistant Examiner*—Sheng Han
(74) *Attorney, Agent, or Firm*—Nelson Mullins Riley & Scarborough, LLP

(57) ABSTRACT

An electroactivated film and methods for its production are described, where the film includes a first electrode that is spaced apart from a second electrode, a water insoluble electrically conductive medium which is permeable to moisture and oxygen, which comprises a water insoluble polymer gel containing an ionic liquid, and which contacts both electrodes, an electrocatalyst which can be reversibly oxidized and reduced and which facilitates the production of a peroxide when an electrical potential is imposed across the electrodes, and optionally a peroxide-activating catalyst which converts the peroxide to an activated peroxide.

16 Claims, 6 Drawing Sheets

U.S. PATENT DOCUMENTS

| | | | |
|---|---|---|---|
| 6,100,394 | A | 8/2000 | Collins et al. ............... 540/467 |
| 7,166,555 | B2 | 1/2007 | Shustack et al. ............ 502/159 |
| 2001/0031243 | A1* | 10/2001 | Unger ........................ 424/9.51 |
| 2003/0073005 | A1* | 4/2003 | Kim et al. .................... 429/326 |
| 2004/0134857 | A1 | 7/2004 | Huling et al. |
| 2004/0267169 | A1 | 12/2004 | Sun et al. |
| 2005/0010161 | A1* | 1/2005 | Sun et al. ....................... 604/20 |
| 2005/0034978 | A1* | 2/2005 | Kazi et al. .................. 204/267 |
| 2005/0112810 | A1 | 5/2005 | Kobayashi |
| 2005/0215871 | A1 | 9/2005 | Feldman et al. |
| 2005/0263182 | A1 | 12/2005 | Morooka et al. |
| 2006/0072182 | A1* | 4/2006 | Oh et al. ...................... 359/265 |
| 2006/0191686 | A1 | 8/2006 | Blauch et al. |
| 2007/0278109 | A1 | 12/2007 | Kendig et al. |
| 2009/0191357 | A1* | 7/2009 | Moore et al. ................ 427/551 |

FOREIGN PATENT DOCUMENTS

| | | | |
|---|---|---|---|
| EP | 0339371 | * | 12/1989 |
| FR | 2548167 | A1 | 1/1985 |
| WO | 9011120 | A1 | 10/1990 |
| WO | WO 0200267 | * | 3/2002 |
| WO | WO 2004/099754 | A2 | 11/2004 |
| WO | 2008/018856 | A2 | 2/2008 |
| WO | 2008/018856 | A3 | 2/2008 |
| WO | 2008018856 | A1 | 2/2008 |

OTHER PUBLICATIONS

Reiter et al. "Ternary Polymer Electrolytes with 1-methylimidazole based Ionic Liquids and aprotic solvents" Electrochimica Acta 52 (2006) 1398-1408.*

Katri Vaik, et al., *Oxygen reduction on phenanthrenequinone-modified glassy carbon electrodes in 0.1 M KOH*, Journal of Electroanalytical Chemistry, 564 (2004) 159-166.

Ave Sarapuu, et al., *Electrochemical reduction of oxygen on anthraquinone-modified glassy carbon electrodes in alkaline solution*, Journal of Electroanalytical Chemistry 541 (2003) 23-29.

Malingappagari Pandurangappa, et al., *Homogeneous chemical derivatisation of carbon particles: a novel method for funtionalising carbon surfaces*, Analyst, 2002, 127, 1568-1571.

Marko Kullapere, et al., *Oxygen electroreduction on anthraquinone-modified nickel electrodes in alkaline solution*, Electrochemistry Communications 9 (2007) 1196-1201.

Kaido Tammeveski, et al., *Surface redox catalysis for $O_2$ reduction on quinine-modified glassy carbon electrodes*, Journal of Electroanalytical Chemistry, 515 (2001) 101-112.

Katri Vaik, et al., *Electrocatalytic oxygen reduction on glassy carbon grafted with anthraquinone by anodic oxidation of a carboxylate substituent*, Electrochimica Acta, 50 (2005) 5126-5131.

U.S. Patent and Trademark Office Non-Final Office Action mailed Aug. 7, 2009, U.S. Appl. No. 11/471,877, filed Jun. 21, 2006, Patrick J. Kinlen, et al.

U.S. Patent and Trademark Office Non-Final Office Action mailed Oct. 28, 2008, U.S. Appl. No. 11/471,877, filed Jun. 21, 2006, Patrick J. Kinlen, et al.

Amendment and response to Office Action filed Apr. 28, 2009 with the U.S. Patent and Trademark Office in response to U.S. Patent and Trademark Office Non-Final Office Action mailed Oct. 28, 2008, U.S. Appl. No. 11/471,877, filed Jun. 21, 2006, Patrick J. Kinlen, et al.

U.S. Patent and Trademark Office Non-Final Office Action mailed Oct. 2, 2009, U.S. Appl. No. 12/215,357, filed Jun. 26, 2008, Shifeng Hou, et al.

ISA/US, Patent Cooperation Treaty International Application No. PCT/US06/24091, PCT International Search Report and Written Opinion, completed Aug. 22, 2008, mailed Sep. 8, 2008.

Gupta, Sayam Sen, et al., Rapid and Total Destruction of Chlorophenois by Activated Hydrogen Peroxide, Science, Apr. 12, 2002, vol. 296, No. 5566, pp. 326-328. Abstract, text, para 5.

Khetan, S., et al., New General Purpose Decontamination System for Chemical and Biological Warfare and Terrorism Agents, DTIC ADA451766, Nov. 20, 2003. Abstract.

Response filed Feb. 8, 2010 with the U.S. Patent and Trademark Offce to the outstanding Non-Final Office Action mailed Aug. 7, 2009, U.S. Appl. No. 11/471,877, filed Jun. 21, 2006, Patrick J. Kinlen, et al.

U.S. Patent and Trademark Office, Final Office Action mailed May 11, 2010, U.S. Appl. No. 11/471,877, filed Jun. 21, 2006, Patrick J. Kinlen et al.

Terrence J. Collins, TAML Oxidant Activators: A New Approach to the Activation of Hydrogen Peroxide for Environmentally Significant Problems, Acc. Chem. Res. 2002, 35, 782-790. Copyright 2002 American Chemical Society Published on Web Jun. 12, 2002.

European Patent Office, Invitation to Pay Additional Fees and, Where Applicable, Protest Fee and Partial International Search, mailed Nov. 3, 2009, International Application No. PCT/US2009/044778, International Filing Date May 21, 2009, Applicant Lumimove, Inc., a Missouri Corporation, dba . . . .

K. Ho et al: "Indirect catalytic epoxidation with hydrogen peroxide electrogenerated in ionic liquids", Tetrahedron, vol. 62, May 22, 2006, XP002550798. pp. 6650-6658.

U.S. Patent and Trademark Office Final Office Action mailed Apr. 5, 2010, U.S. Appl. No. 12/215,357, filed Jun. 26, 2008, Shifeng Hou et al.

Patent Cooperation Treaty, International Search Report and Written Opinion, completed Oct. 19, 2009 and mailed Mar. 23, 2010, PCT Patent Application No. PCT/US09/044778, filed May 21, 2009, Lumimove, Inc., a Missouri Corporation, dba Crosslink.

K. Ho et al., Indirect catalytic epoxidation with hydrogen peroxide electrogenerated in ionic liquids, Tetrahedron, vol. 62, 22 May 2006, pp. 6650-6658, XP002550798.

Response filed Jan. 20, 2010 with the U.S. Patent and Trademark Office to the outstanding Non-Final Office Action mailed Oct. 2, 2009, U.S. Appl. No. 12/215,357, filed Jun. 26, 2008, Shifeng Hou, et al.

United States Patent and Trademark Office, Non-Final Office Action, mailed Sep. 27, 2010, U.S. Appl. No. 12/215,359, filed Jun. 26, 2008, Inventor Shifeng Hou, et al.

Response to Final Office Action mailed Apr. 5, 2010, filed Oct. 5, 2010 with the United States Patent and Trademark Office, U.S. Appl. No. 12/215,357, filed Jun. 26, 2008, Inventor Shifeng Hou, et al.

Response to Final Office Action mailed May 11, 2010, filed Oct. 12, 2010 with the United States Patent and Trademark Office, U.S. Appl. No. 11/471,877, filed Jun. 21, 2006, Inventor Patrick J. Kinlen, et al.

* cited by examiner

X= H, R-, Br
Y= H, R-, -NH₂, Cl, -OH
Z= H, R-, -OH, -NH₂

ELECTROACTIVATED FILM WITH POLYMER GEL ELECTROLYTE

CROSS-REFERENCES TO RELATED PATENTS AND PATENT APPLICATIONS

This application is a non-provisional of and claims priority to U.S. Provisional Patent Application 61/128,953, filed May 23, 2008, and is related to U.S. patent application Ser. No. 11/471,877, filed Jun. 21, 2006, which was a non-provisional of U.S. Provisional Patent Application No. 60/692,529, filed Jun. 21, 2005, each of which is incorporated by reference herein in its entirety.

GOVERNMENT LICENSE RIGHTS

This invention was made with Government support under Contract No. W911QY-06-C-0065 awarded by U.S. Army RDECOM Acquisition Center, Natick Contracting Division, Natick, Mass. The government has certain rights in the invention.

BACKGROUND OF THE INVENTION (1) Field of the Invention

The present invention relates to decontaminating coatings, and more particularly to decontaminating coatings in which the decontaminating effect is triggered by electroactivating the coating.

(2) Description of the Related Art

The need to protect or cleanse surfaces of contaminants is important in many different contexts. It is well known that equipment, floors, walls, counters, and the like, in hospitals and health care facilities must be sanitized regularly. Food service equipment and facilities must be cleaned and sanitized. Certain processing equipment in some manufacturing and/or diagnostic facilities demands a high level of cleanliness and freedom from contaminants.

In a different context, it is important to be able to decontaminate or neutralize chemical and biological warfare agents in order to reduce or avoid grave injury or death of human beings. In this context, the purposeful deployment of extremely aggressive and harmful chemical or biological agents is meant to cause massive contamination of exposed surfaces, which can remain dangerous to living subjects for as long as the harmful agent retains its potency and remains on the surface. Not only are organizations such as the armed forces interested in dealing with such harmful agents, but organizations such as post offices, package delivery services, and the like, are also vigilant to such attacks.

Many sanitization and cleaning methods and compounds are well known in the art that meet the needs of common cleaning and sanitizing requirements. More recently, greater attention has been placed on improved and different techniques and compounds that can be used for the decontamination of surfaces and articles contaminated with chemical and biological warfare agents.

In U.S. patent application Ser. No. 11/471,877, Kinlen et al. disclosed a method of producing peroxides in a coating, which comprised providing a coating comprising a peroxide source and a peroxide activating catalyst, causing the peroxide source to produce a peroxide, and contacting the peroxide with the catalyst to produce activated peroxide. That application also disclosed a coating for a surface, wherein the coating comprised a peroxide source and a peroxide activating catalyst in a durable matrix.

SUMMARY OF THE INVENTION

Briefly, the present invention is directed to an electroactivated film that includes a first electrode that is spaced apart from a second electrode, a water insoluble electrically conductive medium which is permeable to moisture and oxygen and which contacts both electrodes, an electrocatalyst which can be reversibly oxidized and reduced and which facilitates the production of a peroxide when an electrical potential is imposed across the electrodes, and optionally a peroxide-activating catalyst which converts the peroxide to an activated peroxide; and the novel improvement wherein the water insoluble electrically conductive medium which is permeable to moisture and oxygen comprises a water insoluble polymer gel containing an ionic liquid.

The present invention is also directed to a novel electroactivated film comprising a first electrode that is spaced apart from a second electrode, a water insoluble electrically conductive medium which is permeable to moisture and oxygen and which contacts both electrodes, an electrocatalyst which can be reversibly oxidized and reduced and which facilitates the production of a peroxide when an electrical potential is imposed across the electrodes, and optionally a peroxide-activating catalyst which converts the peroxide to an activated peroxide, wherein the water insoluble electrically conductive medium which is permeable to moisture and oxygen comprises a water insoluble polymer gel containing an ionic liquid.

The present invention is also directed to a method of producing an electroactivated film that includes a first electrode that is spaced apart from a second electrode, a water insoluble electrically conductive medium which is permeable to moisture and oxygen and which contacts both electrodes, an electrocatalyst which can be reversibly oxidized and reduced and which facilitates the production of a peroxide when an electrical potential is imposed across the electrodes, and optionally a peroxide-activating catalyst which converts the peroxide to an activated peroxide; where the method includes the novel improvement comprising forming the water insoluble electrically conductive medium which is permeable to moisture and oxygen by crosslinking a polyvinyl alcohol/amine copolymer with a polymer selected from carboxymethyl cellulose, polyvinyl alcohol and polyethylene oxide in the presence of an ionic liquid to form a polymer electrolyte gel.

DETAILED DESCRIPTION OF THE PREFERRED EMBODIMENTS

Figure 1:
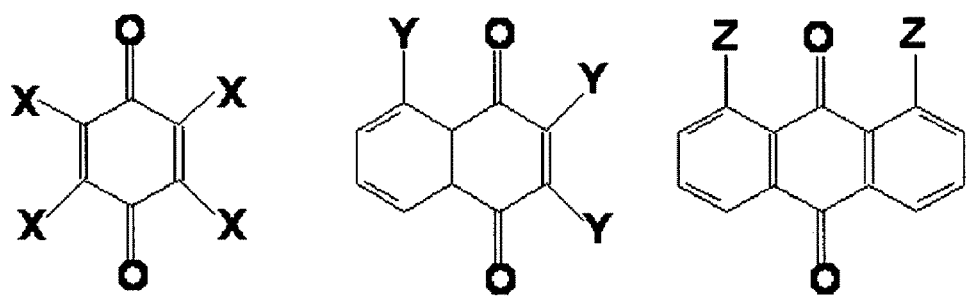
FIG. 1 shows examples of substituted anthraquinones that are useful as the electrocatalyst in an embodiment of the present method.

In accordance with the present invention, it has been discovered that hydrogen peroxide can be produced in a film from oxygen and water when an electric potential is applied to the film. A great advantage of the novel film is that the oxygen and water that are used to form the decontaminating agent can be replenished by simple contact of the film with water and oxygen—both of which can be provided by moist ambient air. This feature permits repeated use of the film for decontamination purposes without further addition of reactants and without the necessity of storing a source of the active agent or its precursor within the film. Therefore, the coating can be thin and light and can be activated, restored by exposure to air and water, and re-activated again and again. This feature is very advantageous when the coating is difficult to reach or is used in areas where it is difficult or dangerous to renew a surface treatment between contaminating events.

The present electroactivated film includes a first electrode that is spaced apart from a second electrode. A water insoluble electrically conductive medium which is permeable to moisture and oxygen contacts both electrodes and serves as a conductor between the electrodes to complete an electrical circuit and also can act as a temporary reservoir of moisture and oxygen. Preferably, the film also includes an electrocatalyst, which is a chemical that can be reversibly oxidized and reduced and which facilitates the production of a peroxide when an electrical potential is imposed across the electrodes. Optionally, the film includes a peroxide-activating catalyst, which converts the peroxide to an activated peroxide in order to increase its activity against chemical contaminants.

The film can also include a lead to each electrode, which connects the electrode to a positive or negative pole of a source of an electrical potential such as a battery, generator, or line voltage. A switch can be placed in the circuit to control the imposition of an electrical potential to the film.

The present film can be used as a stand-alone film, or it can be applied to a surface as a coating. When used as a coating, the film can be adapted to be used on the surfaces of almost any type of substrate. Examples of substrates on which the present coatings can be applied include metal, plastic, wood, fabric, glass, ceramic, or a mixture of any of these. The present films and methods are particularly useful when applied to the surfaces of flexible substrates, such as fabrics and plastic films. In these applications, the present protective coating can be applied to clothing, tents, protective shelters, and the like.

Although almost any substrate is suitable for use with the present coatings and methods, it is preferred that the substrate is one that has a surface that is subject to contamination, such as a surface that is exposed to the environment. The substrate can be hard, soft, or of almost any texture, and can be composed of almost any material, including, without limitation, metal, plastic, wood, fabric, clay, fibers, paper, or the like. Substrates on which the present coatings and methods are commonly useful include tents, protective coverings and shelters, outer surfaces of vehicles and equipment that may be exposed to harmful agents, such as nerve gases, toxins, and biological warfare agents, and surfaces for which cleanliness and sterility are important, such as on food preparation and food service equipment and hospital and health service equipment. Furthermore, the coatings and methods of the present invention can be applied over almost any pre-coat that has been applied to a substrate surface, such as a painted surface.

When the term "surface", or "surfaces", is used herein in relation to a substrate—a material or article on which the subject coating is placed —it means any surface of the material or article that is subject to contamination and for which a decontamination ability is desired. These surfaces are commonly outer surfaces, that is, surfaces of the material or article that are exposed to the surrounding environment. When the term "surface" is used herein in relation to the present coating, it refers to the outer surface of the coating, rather than to the surface of the coating that contacts the substrate or is nearest the substrate.

As used herein, the terms "electroactivated film" mean a film that displays decontaminating properties when an electrical potential is applied to the film. The application of an electrical potential to the film in order to generate a decontaminating agent is referred to herein as "electroactivation". Preferably, the film displays the decontaminating properties to a greater degree during and/or after electroactivation than before electroactivation. In one embodiment, the electroactivated film produces a decontaminating agent, such as hydrogen peroxide, when an electrical potential is applied to the coating.

As used herein, the term "contaminant" means any chemical or biological compound, constituent, species, or agent that through its chemical or biological action on life processes can, if left untreated, cause death, temporary incapacitation, or permanent harm to humans or animals. This includes all such chemicals or biological agents, regardless of their origin or of their method of production. The present method and coating is useful for the decontamination of surfaces that are contaminated with chemical and/or biological warfare agents, as well as with common bacteria, viruses, fungi, or other undesirable chemicals, toxins, or living organisms. Biological warfare agents that can be destroyed by the present invention include, without limitation, bacteria, viruses and fungi, including vegetative and spore forms. These include organisms that produce, or are the causative organisms for, anthrax, smallpox, plague, botulinum toxin, and other diseases. Also included are the chemical toxins that are produced by the organisms.

As used herein, the term "decontaminate" means to change a contaminant from a form or an amount that is harmful to a human or an animal to a form or an amount that is less harmful to the human or animal by any degree. Preferably, when a contaminant is decontaminated, it is rendered substantially harmless to humans or animals that come into contact with it after decontamination is completed. When used herein in the context of decontamination of a contaminant, the term "destroy" means the modification of the chemical structure of the contaminant to a chemical form that is less harmful to humans or animals than the original structure, and the term "neutralize" means the combination of the contaminant with another compound or material that binds or dilutes the contaminant, or otherwise renders it less available to harmful interaction with the biological system of a human or animal with which it comes in contact.

Chemical warfare agents that can be destroyed by the present invention include, but are not limited to, types of nerve gas G, such as the o-alkyl phosphonofluoridates, sarin (GB) and soman (GD), and o-alkyl phophoramidocyanidates, such as tabun (GA); types of nerve gas V, such as o-alkyl, s-2-dialkyl aminoethyl alkylphosphonothiolates and corresponding alkylated or protonated salts, such as VX; vesicants, such as the mustard compounds, including 2-chloroethyl-chloromethylsulfide, bis(2-chloroethyl)sulfide, bis(2-chloroethylthio)methane, 1,2-bis(2-chloroethylthio)ethane, 1,3-bis(2-chloroethylthio)-n-propane, 1,4-bis(2-chloroethylthio)-n-butane, 1,5-bis(2-chloroethylthio)-n-pentane, bis(2-chloroethylthiomethyl)ether, and bis(2-chloroethylthioethyl) ether; Lewisites, including 2-chlorovinyldichloroarsine, bis(2-chlorovinyl)chloroarsine, tris(2-chlorovinyl)arsine, bis(2-chloroethyl)ethylamine, and bis(2-chloroethyl)methylamine; saxitoxin, ricin, alkyl phosphonyidifluoride, alkyl phosphonites, chlorosarin, chlorosoman, amiton, 1,1,3,3,3,-pentafluoro-2-(trifluoromethyl)-1-propene, 3-quinuclidinyl benzilate, methylphosphonyl dichloride, dimethyl methylphosphonate, dialkyl phosphoramidic dihalides, dialkyl phosphoramidates, arsenic trichloride, diphenyl hydroxyacetic acid, quinuclidin-3-ol, dialkyl aminoethyl-2-chlorides, dialkyl aminoethan-2-ols, dialkyl aminoethane-2-thiols, thiodiglycols, pinacolyl alcohols, phosgene, cyanogen chloride, hydrogen cyanide, chloropicrin, phosphorous oxychloride, phosphorous trichloride, phosphorus pentachloride, alkyl phosphites, sulfur monochloride, sulfur dichloride, and thionyl chloride.

Electrodes

The present electroactivated film includes a first electrode that is spaced apart from a second electrode. When it is said that a first electrode is "spaced apart" from a second electrode, it is meant that the electrodes do not touch each other. In some configurations, the electrodes can be separated by approximately the same distance at all points in order to equalize current density and current flow between the electrodes.

The electrodes of the present invention can be composed of any material that is known in the art for use as an electrode. By way of example, metals, metal oxides, intrinsically conductive polymers, carbon, and the like, can be used as electrodes. In particular, titanium, silver, platinum, polyanilines, polypyrroles, polythiophenes, indium tin oxide, carbon, carbon paper, carbon cloth, carbon fibers, carbon ink, glassy carbon, carbon-filled polymers and resins, and the like are useful as electrodes in the present invention. The electrodes can be in the form of strips, sponges, fibers, woven and non-woven textiles, films, wires, rods, bars, screens, and the like. The electrodes can be deployed within the film in a coplanar layer, or they can be arranged in sequential layers within the film.

In some applications, carbon electrodes have been found to be preferred. In particular, it has been found that carbon fiber electrodes result in the generation of higher concentrations of hydrogen peroxide, by at least one order of magnitude, due to higher surface areas than provided by conventional carbon electrodes such as glassy carbon electrodes or screen-printed carbon electrodes. As will be discussed below in detail, modified carbon electrodes, and in particular modified carbon fiber electrodes, that are coated with electrodeposited, physically adsorbed, or covalently bound electrocatalyst compounds have been found to generate twice the amount of peroxide as unmodified carbon fibers without immobilized electrocatalyst. Furthermore, modified carbon electrodes to which the immobilized electrocatalyst is covalently bonded exhibit improved stability with cycling without desorption of the electrocatalyst from the surface, as compared with electrodes having physically adsorbed electrocatalysts.

One or both of the electrodes is optionally coated with a polymer, such as a fluorinated sulfonic acid copolymer, an example of which is Nafion®, in order to reduce or prevent the decomposition of hydrogen peroxide. Preferably, the anode is optionally coated with a fluorinated sulfonic acid copolymer, such as Nafion®.

There can be one or more first electrodes and one or more second electrodes, and each electrode can be formed from the same or a different material and can have the same or a different form as any other electrode. Each "first" electrode will have the same charge as all other first electrodes. In other words, all first electrodes can be either positive electrodes (anodes) or negative electrodes (cathodes). Likewise, each second electrode will have the same charge as all other second electrodes, which charge is opposite in sign from the charge on the first electrodes.

When the present electroactivated film is used as a decontaminating coating, the decontaminating agent can be produced by applying an electrical potential to the film. In order to supply an electrical potential to the present film, the first and second electrodes are preferably connected to opposite poles of a source of an electrical potential by electrode leads. The electrode leads can be of any material that is commonly used for electrode leads in the art. For example, the electrode leads can be formed from a metal, such as silver or copper, or from an electrically conductive metal compound, or from carbon, or from an intrinsically conductive polymer, or the like. The source of electrical potential can be any source of electrical potential, such as, for example, a battery, line voltage, solar panel, electrical generator, or any other source of electrical potential. However, the use of a battery or any other source of DC current is preferred. It is preferred that direct current be applied to the coating at a low voltage. It is preferable that the voltage is between about −10 volts and +50 volts versus a Ag/AgCl reference electrode, more preferred that it is between about −5 volts and about +25 volts vs. Ag/AgCl, even more preferred that it is between about −2 volts and about +5 volts vs. Ag/AgCl, and yet more preferred that it is between about −1 volts and about +2 volts vs. Ag/AgCl.

Electrocatalyst

In embodiments of the present coating where hydrogen peroxide is the decontaminating agent, it is preferred that one or more electrocatalysts are included as components of the film. As used herein, an electrocatalyst is to be understood to be a compound or molecule which facilitates the transfer of electrons and hydrogen ions to oxygen and which promotes the formation of hydrogen peroxide when an electrical potential is imposed across the electrodes. Preferably, the electrocatalyst is a compound that can be reversibly oxidized and reduced. Examples of useful electrocatalysts for the present coating and method comprise substituted or unsubstituted quinones, including naphthoquinones and anthraquinones.

Specific examples of useful quinone electrocatalysts include 2,6-dihydroxyanthraquinone (DHAQ), 2,3-dichloro-1,4-naphthoquinone (DCNQ), aminoanthraquinone (AAQ), tetrabromo-p-benzoquinone (TBBQ), 6,13-pentacenequinone (PAQ), 2-amino-3-chloro-1,4-naphthoquinone (ACNQ), phenanthrenequinone (PTQ), anthraquinone (AQ), and the substituted anthraquinones shown in FIG. 1. Mixtures of any of these can also be used. TBBQ and DHAQ were preferred electrocatalysts.

Figure 2:
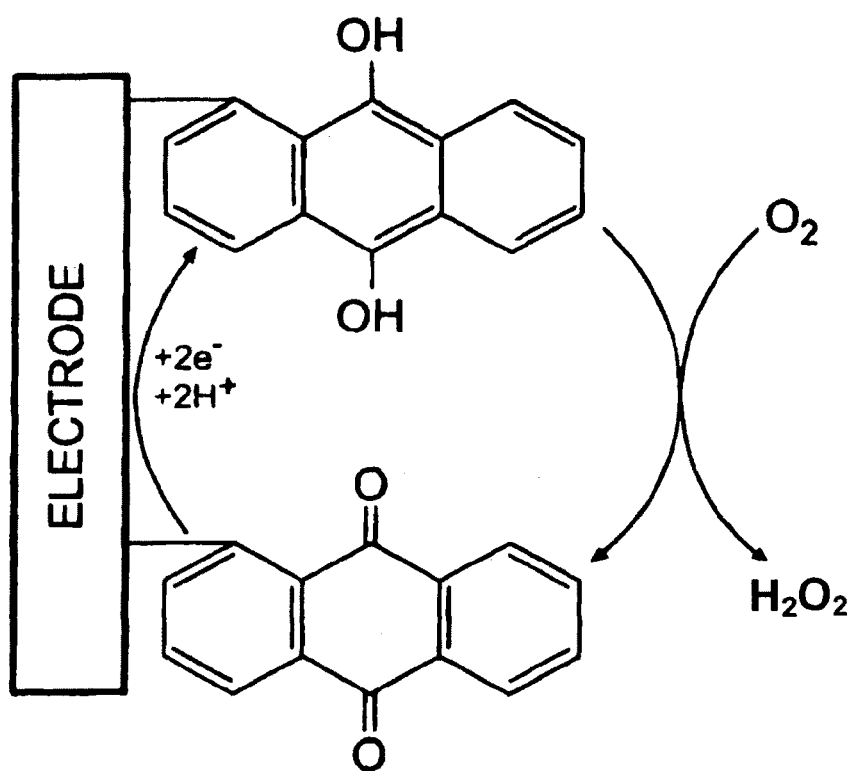
FIG. 2 illustrates the attachment of anthraquinone to an electrode and shows its action in transferring hydrogen ions and electrons in the reaction to produce hydrogen peroxide with the reduction of oxygen in an embodiment of the present method.

The electrocatalyst can be attached to an electrode, or it can be distributed throughout the gel. FIG. 2 illustrates the attachment of anthraquinone to a cathode, which can be a carbon electrode, and also illustrates the function of the anthraquinone in transferring hydrogen ions and electrons from the cathode to oxygen for the production of hydrogen peroxide. In one embodiment, a first electrode with bound anthraquinone could be attached to the substrate and covered with the gel medium layer. A second electrode having opposite polarity could be separated from the first electrode and also be in contact with the gel medium. Imposition of an electrical potential between the electrodes causes the reduction of anthraquinone to 4,9-dihydroxyanthracene. Oxygen diffusing through the gel medium would then be reduced by the 4,9-dihydroxyanthracene to hydrogen peroxide and oxidizes the 4,9-dihydroxyanthracene back to anthraquinone. The cycle could then be repeated for as long as the electrical potential remained imposed on the coating and oxygen was available at the first electrode.

It has been found that the electrocatalyst can be immobilized onto an electrode in order to slow or prevent its diffusion through the gel medium and loss from the film. Immobilization of the electrocatalyst on an electrode can be done by any method that affixes the electrocatalyst to the electrode in such a way that it does not impair the ionic and electron transfer function of the molecule, but reduces or prevents leaching of the electrocatalyst from the film during repeated cycles of use. Preferred methods of immobilizing the electrocatalyst onto an electrode include electropolymerization, physical adsorption, and covalent bonding.

When a quinone is used as the electrocatalyst and the electrode is carbon, the quinone can be physically adsorbed onto the carbon by treating the carbon surface with a mineral acid, such as nitric acid, followed by treating with a base, such as sodium hydroxide or potassium hydroxide, then washing with water, and contacting the washed carbon surface with a solution of the desired quinone in a suitable solvent under conditions of time, temperature and pH sufficient for the quinone to adsorb onto the surface of the carbon. After washing, the quinone-coated electrode is ready for use.

In a particular embodiment, a carbon fiber electrode can be coated with a quinone electrocatalyst by contacting the fiber with 10% by weight nitric acid at room temperature for 2-4 hours, washing with deionized water, contacting the fibers with a 0.1% to about 10% by weight solution of the quinone in ethanol or acetonitrile for 6-12 hours, and then washing the fibers with water and/or an acid solution.

In an alternative aspect, a modified electrode can be produced by intermixing a quinone with a carbon ink and applying the mixture to a surface by screen printing or the like. When the carbon ink is cured, the mixture forms a carbon electrode that includes an immobilized electrocatalyst.

In another alternative aspect, a modified electrode can be produced by forming a dispersion of a quinone and carbon powder in a liquid, such as hexanes. Mixing can be accomplished by high intensity mixing, such as sonication. The dispersion can be spray coated onto a surface to form a carbon/electrocatalyst electrode.

In another alternative aspect, a quinone can also be intermixed with carbon powder in the presence of a binder, such as 10% by weight Nafion® solution, in a solvent, such as 2-propanol. After mixing the binder with the quinone and carbon powder, the solvent can be evaporated to produce a blended powder. The resulting powder can be re-dispersed in hexanes and can be applied to a surface, such as by spray-coating, to form an electrode comprising the quinone electrocatalyst, carbon powder and binder.

In another embodiment, a quinone can be immobilized onto a carbon electrode by covalent bonding. It has been found that advantages can be obtained if carbon fibers are used as the electrode. Covalently attached quinones do not desorb from the electrode during use, and much higher quinone loadings can be obtained on carbon fiber, as opposed to glassy carbon for example, due to the greater surface area per unit weight of the carbon fibers. Carbon fiber electrodes having covalently attached quinone electrocatalysts generate higher concentrations of hydrogen peroxide, by at least an order of magnitude, than glassy carbon or screen printed carbon electrodes. Moreover, carbon electrodes having covalently bound quinone electrocatalysts generate twice the amount of peroxide as pristine carbon electrodes absent the attached quinone.

Covalent attachment of a quinone electrocatalyst to a carbon electrode can be accomplished by any of the methods described by Schiffrin et al., *J. of electroanalytical chemistry*, 515:101 (2001), Schiffrin et al., *J. of electroanalytical chemistry*, 564:159 (2004), Schiffrin et al., *J. of electroanalytical chemistry*, 541:23 (2003), Kullapere et al., *Electrochemistry communications*, 9(5):1196-1201 (2007), Pandurangappa, M. et al., *Analyst*, 127:1568-1571 (2002), or Vaik et al., *Electrochemical Acta*, 50(25-26):5126-5131 (2005).

Figure 3:
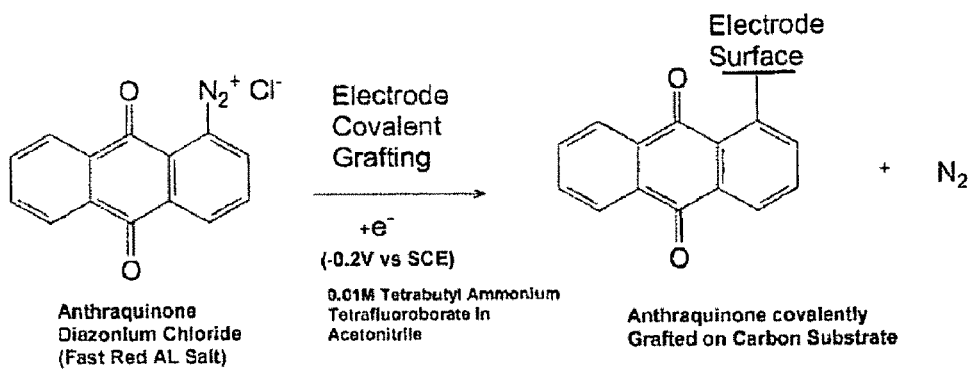
FIG. 3 is a schematic representation of covalent grafting of a quinone onto a carbon electrode.
Figure 4:
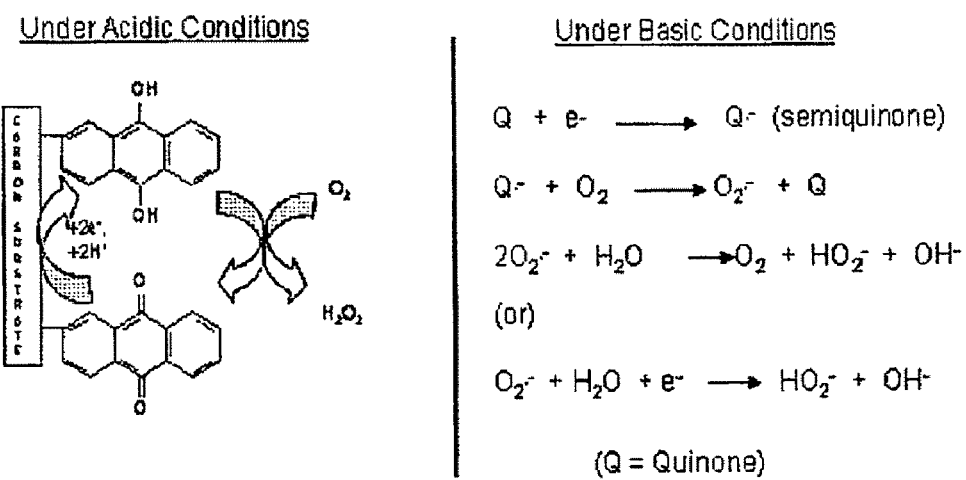
FIG. 4 illustrates possible mechanism of electrochemical generation of peroxide from oxygen using quinone-immobilized carbon electrodes under acidic and basic conditions.

One example of a method of covalently bonding a quinone to a carbon substrate involves grafting diazonium salts of the quinone monomer (e.g. anthraquinone diazonium chloride) onto the carbon. This method is illustrated in FIG. 3, and mechanisms of peroxide generation from oxygen using quinone-immobililized carbon electrodes under acidic and basic conditions are illustrated in FIG. 4. In brief, the method involves placing the electrode into an electrochemical cell holding a solution of the quinone, diazonium chloride and tetrabutyl ammonium tetrafluoroborate in acetonitrile. The quinone is deposited onto the electrode by subjecting the cell to cyclic voltammetry between 0.65 to 0.45 V vs. SCE using Gamry at 200 mV/s scan rate. Covalent grafting is completed by applying a constant potential of −0.2 V vs. SCE for 20 minutes to the coated electrodes.

Figure 5:
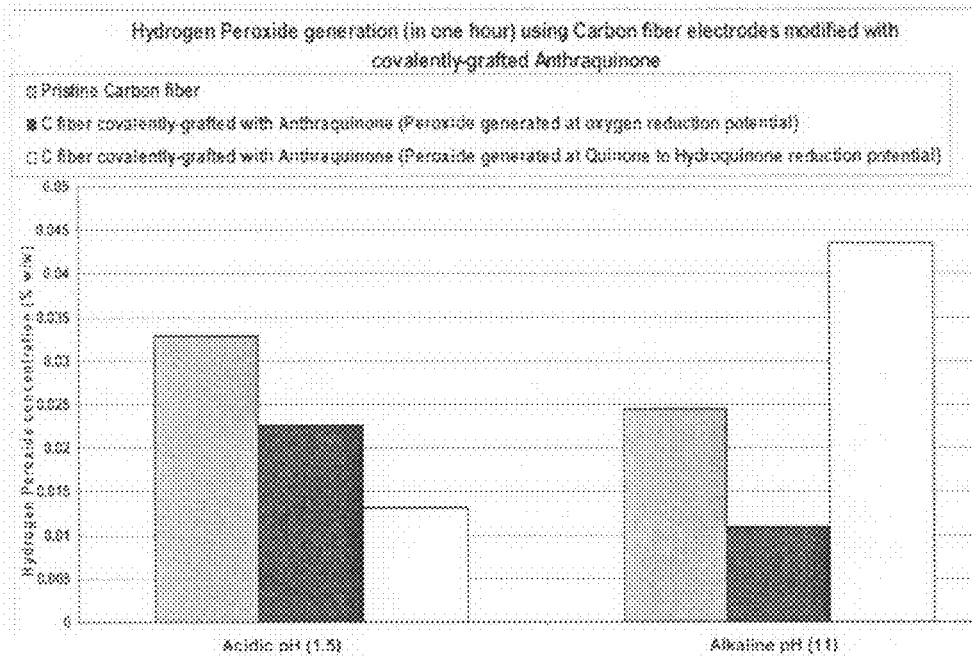
FIG. 5 shows levels of hydrogen peroxide generation in one hour using carbon fiber electrodes modified with covalently-grafted anthraquinone and indicates the preference for $H_2O_2$ generation with covalently grafted quinone at basic pH and a quinone-to-hydroquinone reduction potential.

FIG. 5 shows levels of hydrogen peroxide generation in one hour using carbon fiber electrodes modified with covalently-grafted anthraquinone and indicates the preference for $H_2O_2$ generation with covalently grafted quinone at basic pH and a quinone-to-hydroquinone reduction potential.

Polymer Gel Electrolyte

A component of the present coating is a water insoluble electrically conductive medium which is permeable to moisture and oxygen and which contacts both electrodes and serves as a conductor between the electrodes to complete an electrochemical cell. The medium can also act as a temporary reservoir of moisture and oxygen. This medium can be one or more layers of polymers, gels, resins, or any other structural material that forms a solid, rigid, or gel matrix that is not water soluble after curing, and is durable, as discussed below. It is preferred that the medium is a gel. When it is said that the present conductive medium is electrically conductive, it is meant that the medium is ionically conductive and preferably has an ionic conductivity as measured by AC impedance spectroscopy of at least about $1\times10^{-6}$ S/cm, or at least about $1\times10^{-3}$ S/cm, or higher.

When it is said that the present medium is ionically conductive, it is meant that electrical charges are able to move through the coating as ionic species.

It is preferred that the present conductive medium is adherent to the substrate surface and is durable, at least to the extent that the film, once applied and cured, if curing is required, is resistant to removal due to normal use of the article that has been coated. Furthermore, it is preferred that the conductive medium and the film are not water soluble. As those terms are used herein, a medium is not water soluble if not over 2% by weight of the cured medium dissolves upon submersion in water at 25° C. for 24 hours. It is preferred that not over 1% of the medium dissolves, and more preferred that not over 0.5% by weight of the medium dissolves under those conditions. In a preferred embodiment, the present medium is used to form a film that is distinguished from a temporary coating that can be formed on a surface by the application of a foam, a liquid formulation, or the like to the surface.

As mentioned above, when the present film is an electro-activated coating that produces hydrogen peroxide as the decontaminating agent, it is preferred that the medium is permeable to water vapor and oxygen. It is preferred that the present medium is sufficiently permeable to water vapor that it is capable of absorbing at least about 2% of its weight as moisture (water), or at least about 4% of its weight as moisture, or at least about 8% of its weight as moisture, or at least about 10% of its weight as moisture, all from ambient air at about 50% relative humidity. Alternatively, such moisture levels can be provided by applying liquid water or water vapor to the film.

Furthermore, it is preferred that the medium is sufficiently permeable to hydrogen peroxide to permit the migration of hydrogen peroxide to the peroxide activating catalyst and to permit activated hydrogen peroxide to migrate toward the surface of the film so that the activated hydrogen can contact a contaminant that is present on the surface.

In one embodiment, the water insoluble electrically conductive medium which is permeable to moisture and oxygen comprises a water insoluble polymer gel and an ionic liquid. In some embodiments, the gel is a crosslinked polymer gel. In an embodiment of the invention, the gel can include poly(vinyl alcohol)-co-amine (PVA-co-amine), poly(vinyl alcohol)/vinyl formamide (PVANF), a polymer selected from carboxymethyl cellulose (CMC), carboxypropyl cellulose (CPC), carboxyethyl cellulose (CEC), poly(vinyl alcohol) (PVA), poly(ethylene oxide) (PEO), and mixtures thereof, in combination with an ionic liquid and with an optional crosslinking agent.

Examples of polymer gels that are useful in the present invention include an ionic liquid in combination with Poly(vinyl alcohol) (PVA)/H$_3$PO$_4$ gels, NAFION®/H$_2$SO$_4$ gels, PVA/poly(vinyl alcohol)/amine copolymer (PVA-co-amine) gels, PVA/Poly(ethylene oxide) (PEO)/PVA-co-amine gels, and PEO/PVA-co-amine gels. Optionally, the gels can contain other components such as crosslinking agents. A preferred gel comprises PVA/PVA-co-amine with an ionic liquid and a crosslinking agent. Another preferred gel comprises PEO/PVA-co-amine with an ionic liquid and a crosslinking agent. Although almost any crosslinking agent can be used that is chemically compatible with the components of the gel electrolyte, styrene/maleic anhydride and polyamide/epichlorohydrin crosslinkers are preferred.

The poly(vinyl alcohol)/amine copolymer (PVA-co-amine) can be one having the structure:

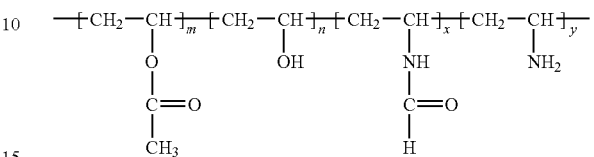

where the value of m plus n ranges from about 1,000 to about 100,000, and in particular from about 1,000 to about 10,000, or from about 1,000 to about 4,000; and where the ratio of m and n is from about 99 to 1 to about 1 to 99, or from about 99 to 1 to about 2 to 1, or from about 20 to 1 to about 5 to 1.

Alternatively, the poly(vinyl alcohol) amine copolymer (PVA-co-amine) can be one having the structure:

$$-[CH_2-CH]_m-[CH_2-CH]_n-[CH_2-CH]_x-[CH_2-CH]_y-$$
$$\quad\quad\quad | \quad\quad\quad\quad | \quad\quad\quad\quad | \quad\quad\quad\quad |$$
$$\quad\quad\quad O \quad\quad\quad\quad OH \quad\quad\quad NH \quad\quad\quad NH_2$$
$$\quad\quad\quad | \quad\quad\quad\quad\quad\quad\quad\quad\quad\quad |$$
$$\quad\quad\quad C{=}O \quad\quad\quad\quad\quad\quad\quad C{=}O$$
$$\quad\quad\quad | \quad\quad\quad\quad\quad\quad\quad\quad\quad\quad |$$
$$\quad\quad\quad CH_3 \quad\quad\quad\quad\quad\quad\quad\quad H$$

where:
m is 0-15 mole %
n is 50-99 mole %
x is 0-30 mole %, preferably 0.5-10 mole %, and
y is 0.2-50 mole %, preferably 1-25 mole %.

Preferably, m is 0-2 mole %, n is 70-95 mole %, x is 0.5-10 mole %, and y is 1-25 mole %. Or, m is 0-2 mole %, n is 85-95 mole %, x is 0.5-4 mole %, and y is 5-12 mole %.

Suitable polyvinyl alcohol/amine copolymers can be purchased commercially and examples of such materials include materials available from Erkol, S. A., Tarragona, Spain having designations: ERKOL™ L12 and M12, as described in U.S. Pat. No. 7,166,555. PVA-co-amines suitable for use in the present invention are also described in U.S. Pat. Nos. 5,326,809, 4,774,285, and EP 0,339,371 A2.

Poly(vinyl alcohols) that are useful in the present medium include almost any poly(vinyl alcohol) of commercial grade and purity. Examples include Celvole® PVA's available from Celanese Corporation, Dallas, Tex., and PVA 98% hydrolyzed, available from Sigma-Aldrich, St. Louis, Mo.

Poly(ethylene oxides) (PEO) that are useful in the present medium include polymers of normal commercial purity and grade having molecular weights from about 100,000 to about 10,000,000. PEO having a molecular weight of from about 1,000,000 to about 9,000,000 is preferred, from about 6,000,000 to about 9,000,000 is more preferred, and about 8,000,000 is yet more preferred. Suitable PEO for use in this invention is available from Dow Chemical Company, DuPont, BASF, and Aldrich, among other suppliers.

It has been found useful to include an ionic liquid as a component of the present electrolyte gel. Although the ionic liquid can be present in the gel at almost any concentration that provides the desired level of conductivity and the desired gel physical parameters, it is normal that the ionic liquid is present in a range of from about 0.1% to about 20%, by volume of the gel, or from about 1% to about 6%, or from about 2% to about 4%. The presence of the ionic liquid increases the ionic conductivity of the gel medium and also appears to add a separate biocidal effect in the decontaminating action of the film.

Examples of ionic liquid that can be used in the present film include ethylammonium nitrate, mixtures of 1,3-dialkylimidazolium or 1-alkylpyridinium halides and trihalogenoaluminates, salts of hexafluorophosphate, salts of tetrafluoroborate, salts of bistriflimide, 1-ethyl-3-methyl imidazolium bis(trifluoromethanesulfonyl) amide, 1-butyl-3-methylimidazolium nitrate, 1-butyl-3-methylimidazolium tetrafluoroborate, 1-butyl-3-methylimidazolium chloride, 1-butyl-3-methylimidazolium hexafluorophosphate, protonated betaine bis(trifluoromethanesulfonyl)imide, N-butyl-N-methyl pyrrolidinium bis(trifluoromethanesulfonyl)imide, ammonium and halide salts of 1-alkyl-3-methylimidazolium, ammonium and halide salts of 1-alkylpyridinium, ammonium and halide salts of N-methyl-N-alkylpyrrolidinium, formate salts, alkylsulfate salts, alkylphosphate salts, glycolate salts, 1-alkylimidazole, and mixtures thereof.

Preferred ionic liquids comprise 1-butyl-3-methylimidazolium hexafluorophosphate ($BMIPF_6$), and 1-butyl-3-methylimidazolium tetrafluoroborate ($BMIBF_4$).

It has been found that gels that are used in embodiments where they are in contact with a hydrogen peroxide activating catalyst such as TAML® preferably have a pH that is from about neutral to basic. Preferred pH ranges are between about 7 and about 12, or between about 7 and about 11, or about 7 and about 10, or about 7 and about 9, or about 8. The pH of the gel can be adjusted by contacting the cured gel with a basic solution to raise the pH into the desired range. For example, a NAFION®/$H_2SO_4$ gel can be contacted with a liquid solution of NaOH to bring the pH above 7. The pH of a gel comprising PVA/PVA-co-amine and $BIMPF_6$ was about 8.

The polymer electrolyte gel of the present invention can be produced by any method known in the art for the production of a gel. A useful method for producing the present gel medium is to intermix the polymer components of the gel with a solvent to form a solution and then to remove the solvent to form a solid or semi-solid gel. If a crosslinking agent is included in the formulation, it can be made to react by application of heat, change of pH, application of radiation, application of a chemical catalyst, removal of solvent, or some other impetus, to form a crosslinked gel.

Almost any crosslinking agent can be used to crosslink the polymers into a gel structure. Examples of suitable crosslinking agents include multifunctional carbodiimides, aldehydes, anhydrides, epoxies, imidates, isocyanates, melamine formaldehyde, epichlorohydrin, polyamide/epichlorohydrin, 2,5-dimethoxytetrahydrofuran, and 2-(4-dimethylcarbomoyl-pyridino)ethane-1-sulfonate. Examples of commercially available polyamide/epichlorohydrin crosslinking agent are the POLYCUP® series of crosslinkers supplied by Hercules, Inc., Wilmington, Del. POLYCUP® 172 has been found to be particularly useful as a crosslinker for the present conductive gels. POLYCUP® 172 can be included in gel formulation and then activated by heating the mixture to about 100° C. to form a crosslinked gel.

An example of the present polymer gel electrolyte comprises from about 0.2% to about 20%, preferably about 4% to about 5% by weight PVA, from about 0.2% to about 20%, preferably about 4% to about 5% by weight PVA-co-amine, from about 0.2% to about 40%, preferably about 5% to about 10% by volume, $BMIPF_6$, wherein the polymers are crosslinked with from about 0.02% to about 2%, preferably about 1.6% by weight of a polyamide/epichlorohydrin crosslinking agent, all based on the weight or volume of the conductive gel.

Another example of the present crosslinked polymer gel comprises from about 0.2% to about 20%, preferably about 2% by weight PEO, from about 0.1% to about 10%, preferably about 1% by weight PVA-co-amine, from about 0.2% to about 40%, preferably about 2% to about 4% by weight $BMIPF_6$, wherein the polymers are crosslinked with from about 0.02% to about 2%, preferably about 0.2% by weight of a polyamide/epichlorohydrin crosslinking agent, all based on the weight or volume of the conductive gel.

Another example of the present crosslinked polymer gel comprises from about 0.2% to about 20%, preferably about 1.6% by weight PEO, from about 0.1% to about 10%, preferably about 0.8% by weight PVA-co-amine, from about 0.2% to about 40%, preferably about 2% to about 20% by volume $BMIBF_4$, wherein the polymers are crosslinked with from about 0.02% to about 2%, preferably about 0.2% by weight of a polyamide/epichlorohydrin crosslinking agent, all based on the weight or volume of the conductive gel.

Peroxide Activating Catalyst

Decontaminating agents of the present invention include hydrogen peroxide and one or both of its deprotonated forms, and activated hydrogen peroxide is particularly preferred. Activated hydrogen peroxide is typically hydrogen peroxide or one of its anionic forms bound to a peroxide activating catalyst. It is believed that the resulting complex of the peroxide with the peroxide activating catalyst is better able to destroy contaminants through one or more of the following reactions: peroxidation, oxidation, perhydrolysis, and hydrolysis.

In order to obtain activated peroxide, it is preferable to include a peroxide activating catalyst in the present film. Examples of useful peroxide activating catalysts include complexes of ethylenediaminetetraacetic acid with metals such as iron (EDTA/Fe complexes), tetraamidomacrocyclic ligand (TAML®) complexes with metals such as iron (TAML®/metal complexes are exemplified by the compounds described in U.S. Pat. Nos. 5,847,120, 6,051,704, 6,011,152, 6,100,394 and 6,054,580), manganese gluconate, sodium hypochlorite, N-[4-(triethylammoniomethyl)benzoyl]-caprolactam chloride, nonanoyloxybenzene sulfonate, porphyrins, phthalocyanines, ruthenium oxide, indium oxide, quinones, and the like. Peroxide activating catalysts of the present invention include TAML®/metal complexes, and TAML®/Fe complexes.

The peroxide activating catalyst can be located anywhere in the present film. For example, it could be distributed throughout the electrically conductive medium, immobilized by ionic bonding in a surface layer formed over the top of the electrically conductive medium, or immobilized on a resin, such as an ion-exchange resin, that can be located in the film at a particular location or distributed throughout the medium. As used herein with respect to the peroxide activating catalyst, the term "immobilized" refers to a catalyst that has been made more resistant to leaching or other removal from the film, such as by physical adsorption, ionic bonding or covalent bonding with another film component, compared with the same non-immobilized catalyst.

Alternatively, the peroxide activating catalyst can be linked to, adsorbed onto, or otherwise affixed to the substrate over which the coating is applied or to either or both of the electrodes.

In one embodiment, the peroxide activating catalyst is immobilized by chemically linking it to the gel by a chemical linkage, or by electrostatic force, or by adsorption into pores. A chemical linkage between the peroxide activating catalyst and the gel can be formed by any of several chemical linkage methods known in the art. An important feature of such a linkage is the stability or inertness of the linkage, and the conjugates forming the linkage, to oxidation by hydrogen peroxide under the conditions found in the activated coating. Stability is provided by alkane- or amide-based linkers that join the catalyst to the gel, and amine and carboxylic acid groups form the basis of many suitable catalyst/gel or catalyst/polymer conjugates, as will alkanes derived from intermediates that comprise substituted olefins.

Examples of methods that are useful for chemically linking the catalyst to the gel include: (a) reaction of a benzylchloride (on the gel) with a primary amine (pendant from ligand or complex of the catalyst) to give a secondary amine, which may be further reacted to give a hindered tertiary amine or quaternary amine for enhance stability or inertness; (b) reaction of a benzoic acid moiety (in a gel) with a carboxylic acid or a nitrile pendent from the catalyst or a ligand attached to the catalyst. Other such linking methods are well known in the art.

In an alternate approach, when the peroxide activating catalyst comprises TAML®, which has an anionic (negatively charged) ionization state, it can be ionically bound with either an anionic ion-exchange resin or with a positively charged (cationic) polymer to immobilize it in the present film.

Figure 6:
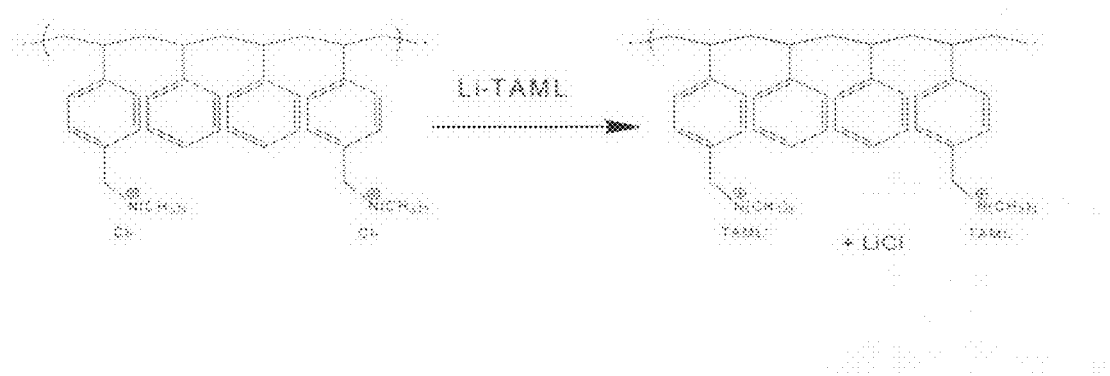
FIG. 6 illustrates the immobilization of TAML® onto anion exchange resin by ionic bonding.

By way of example, TAML® can be immobilized on an anionic ion-exchange resin by replacing the anions present on the resin with TAML®. In one method, TAML® having a negative charge can be contacted in aqueous media with Dowex® 1×2-200 mesh strong base resin at room temperature for a time sufficient for the anions originally on the resin (usually either Cl⁻ or OH⁻) to be replaced, at least to some degree, by TAML®. A schematic representation of this method is shown in FIG. 6.

Figure 7:
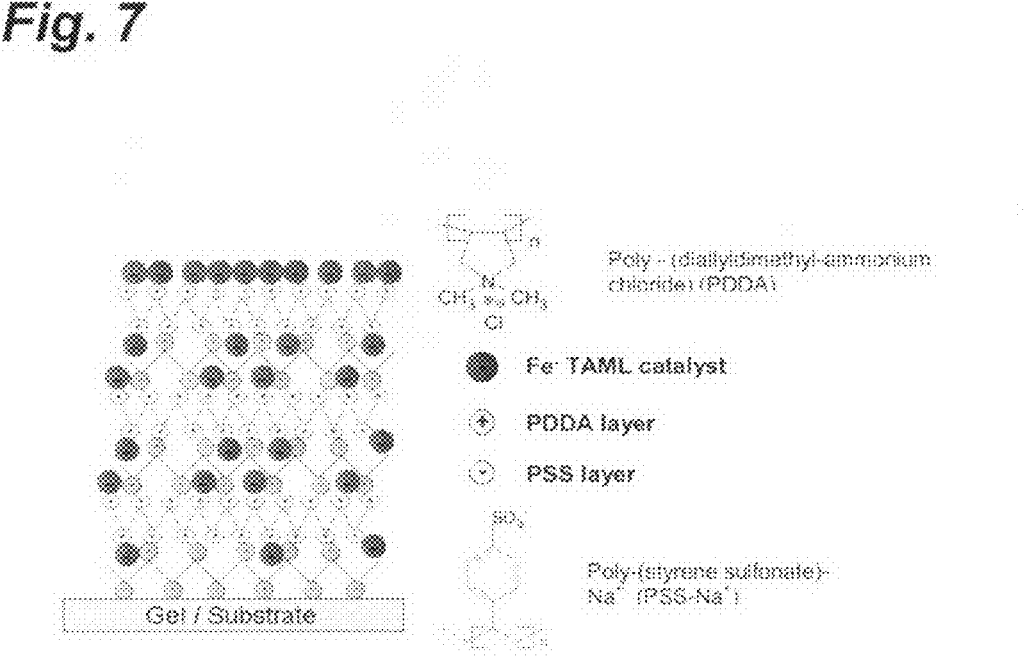
FIG. 7 illustrates the PSS/PDDA-TAML® multilayer immobilization scheme for TAML®.

In another alternate approach for TAML® immobilization, it has been found that a multi-layer structure comprising sequential layers of polystyrene sulfonate (PSS) and a cationic polymer such as poly(diallyidimethylammonium chloride) (PDDA) is capable of binding TAML® when it is applied along with the polymer layers or on top of the multi-layer structure after its formation. A schematic representation of the multi-layer structure is shown in FIG. 7.

Cationic polymers that are suitable for the present invention include quaternized cellulose derivatives, polymeric dimethyidiallylammonium salts and copolymers thereof, polysiloxanes with quaternary groups, diquaternary polydimethylsiloxanes, cationic guar derivatives, polymeric dimethyidiallylammonium salts and their copolymers with esters and amides of acrylic acid and methacrylic acid, dimethyldiallylammonium chloride-acrylamide copolymer, copolymers of vinylpyrrolidone with quaternized derivatives of dialkylamino acrylate and methacrylate, diethyl sulfate-quaternized vinylpyrrolidone-dimethylamino methacrylate copolymers, vinylpyrrolidone-methoimidazolinium chloride copolymers, quaternized polyvinyl alcohol, and mixtures thereof. Poly (diallyldimethylammonium chloride) (PDDA) is preferred.

Figure 8:
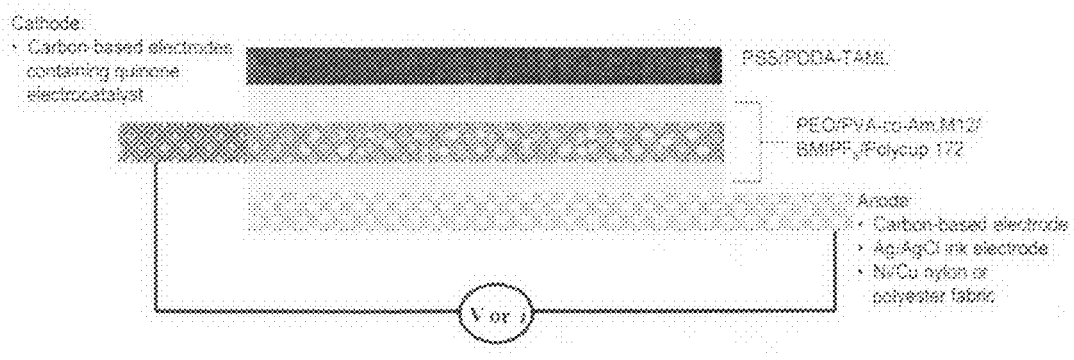
FIG. 8 is a schematic representation of a stacked layer configuration for an embodiment of the present film.

This multi-layer structure that contains immobilized TAML® can be located as a layer on top of the polymer electrolyte gel as shown, for example, in FIG. 8.

The multi-layer TAML®-containing coating can be produced by sequential application of alternating layers of PSS and PDDA on top of the electrolytic gel. Although any number of layers can be used, it is preferred that the coating is formed with at least three repeating layers of PSS/PDDA, starting from the top of the electrolytic gel. In other words, a preferred PSS/PDDA-TAML® layer would contain layers of PSS/PDDA/PSS/PDDA/PSS/PDDA, in sequence upward from the top of the gel. The topmost layer would be a PDDA layer.

TAML® can be added to this coating merely by dropping a solution of TAML® onto the top of the coating and permitting it to soak into the film. A suitable TAML® solution in water can have a TAML® concentration of about 0.1 µM. Typically, a sufficient amount of TAML® is used to catalyze the formation of activated peroxide from substantially all of the perioxide that reaches the PSS/PDDA-TAML® layer. In some instances TAML® is applied to the coating at a rate of from about 0.001 µg/cm² to about 10 µg/cm², based on the surface area of the coating that is treated with TAML®, or from about 0.01 µg/cm² to about 1 µg/cm², or from about 0.01 µg/cm² to about 0.1 µg/cm².

In certain applications, it may be useful to apply a further layer of the polymer electrolyte gel over the top of the PSS/PDDA-TAML® layer in order to enhance the effectiveness of the film against microbes and spores.

Stacked Layer Structure of the Present Film:

Although the present film can have any one of a number of different configurations of the electrodes, the conductive medium and the PSS/PDDA-TAML® layer, if one is applied, it has be found to be useful to arrange the components of the film in a stacked layer structure. A schematic of this arrangement is shown in FIG. 8. It has been found that this arrangement provides advantages of improved manufacturability, decreased device resistance and enhanced $H_2O_2$ generation capacity compared with a film having electrodes arranged side-by-side in a coplanar pattern.

One method of fabrication of the stacked layer structure involves depositing a quinone electrocatalyst onto cured carbon ink, carbon paper or carbon cloth electrodes and immobilizing the quinone onto the electrode by either physical adsorption or by covalent bonding as discussed above to form an electrocatalyst-modified electrode. Alternatively, the quinone electrocatalyst can be mixed with a carbon ink followed by screen printing, or mixing with carbon powder and forming an electrocatalyst-modified electrode by spray coating, or the like, as described earlier.

The novel film can be fabricated by applying a first electrode to a substrate, if one is employed, applying a polymer electrolyte gel layer over the first electrode, applying a second electrode over the polymer electrolyte gel layer, applying a second polymer electrolyte gel layer over the second electrode, and finally applying a PSS/PDDA-TAML® layer over the second gel layer. In one aspect of the film, the electrocatalyst-modified electrode can serve as the cathode and can be the second electrode.

Several embodiments of the stacked layer arrangement included examples having the following components:

| ANODE | GEL | CATHODE |
|---|---|---|
| Carbon cloth | PEO/PVA-co-amine/BMIPF₆/Polycup ® 172 gel | Carbon cloth |
| Carbon ink on fabric | Same | Carbon cloth |
| Ni/Cu polyester cloth | Same | Carbon cloth |
| Carbon cloth | Same | TBBQ-modified carbon paper |
| Carbon ink on fabric | Same | TBBQ-modified carbon paper |
| Ni/Cu polyester cloth | Same | TBBQ-modified carbon paper |
| Carbon ink on fabric | Same | TBBQ/carbon ink printed on gel |
| Ag/AgCl ink on fabric | Same | Carbon fibers |
| Ag/AgCl ink on fabric | Same | TBBQ-modified carbon ink printed on gel |
| Carbon cloth | Same | TBBQ-modified carbon cloth |

After deposition of the first electrode, the anode in this example, the polymer electrolyte gel was flowed onto the surface of the anode and crosslinked by heating it to 100° -120° C. for about 30 to about 60 minutes to form a film. Usually, three layers of the gel were deposited on the surface of the anode. The cathode material was then placed on top of the gel layers and an additional three layers of gel solution were deposited on top of the cathode and crosslinked as for the first layers.

Optionally, additional layers could be added to this arrangement. For example, separator layers (glass fiber filter, micropore filter, Gore® sheet separator, Teslin® sheet separator, and Nafion® film) could be added between the electrode layers in order to reduce or prevent shorting.

Examples of these devices included the following:

| ANODE | SPACER | GEL | CATHODE |
|---|---|---|---|
| Carbon ink printed on fabric | Glass fiber filter | PEO/PVA-co-amine/BMIPF$_6$/Polycup ® 172 gel | TBBQ-modified carbon paper |
| Carbon ink printed on fabric | Micropore filter | Same | TBBQ-carbon ink printed on gel |
| Carbon ink printed on fabric | Micropore filter | Same | TBBQ-modified carbon paper |
| Carbon ink printed on fabric | Nafion ® film | Same | TBBQ-modified carbon paper |
| Carbon cloth | Teslin ® separator | Same | TBBQ-modified carbon cloth |
| Carbon cloth | Gore ® separator | Same | TBBQ-modified carbon cloth |
| Carbon cloth laminated onto fabric | Gore ® separator | PEO/PVA-co-amine/BMIBF$_4$/Polycup ® 172 gel | TBBQ-modified carbon cloth laminated onto fabric |
| Carbon cloth | Teslin ® separator | Same | TBBQ-modified carbon cloth |
| Carbon cloth spray coated with carbon powder | Gore ® separator | Same | TBBQ-modified carbon cloth spray-coated with TBBQ/carbon powder |

Making and Using the Present Film:

The present electroactive films can be produced by any technique that is suitable for the formation of the structures that are described herein. In one embodiment, an electroactivated film is produced by providing a first electrode, which can be a stand-alone material or a material that is deposited onto a substrate, where the first electrode is spaced apart from a second electrode. Applying a water insoluble electrically conductive medium which is permeable to moisture and oxygen in a location where it contacts both electrodes and preferably covers the surfaces of both electrodes. Adding to the film an electrocatalyst which can be reversibly oxidized and reduced and which facilitates the production of a peroxide when an electrical potential is imposed across the electrodes. And covering the topmost layer of the film with a peroxide-activating catalyst which converts the peroxide to an activated peroxide.

In particular aspects of the invention, the water insoluble electrically conductive medium which is permeable to moisture and oxygen can be formed by crosslinking a polyvinyl alcohol/amine copolymer with a polymer selected from carboxymethyl cellulose, polyvinyl alcohol, polyethylene oxide, or a mixture thereof in the presence of an ionic liquid to form a gel.

In another aspect, the electrocatalyst which can be reversibly oxidized and reduced and which facilitates the production of a peroxide when an electrical potential is imposed across the electrodes is immobilized by physical adsorption onto an electrode or by covalent bonding to an electrode.

In another aspect, the elements of the film are arranged in a stacked layer design comprising a first electrode, a gel layer, a second electrode, a gel layer, and a PSS/PDDA-TAML® multi-layer. Optionally, a final gel layer of PEO/PVA-co-amine/BMIPF$_6$/Polycup® 172 can be added.

In another aspect, the peroxide activating catalyst is immobilized by either ionic adsorption onto an anion exchange resin which can be distributed within the electrolytic gel, or placed anywhere else in the film, or by ionic bonding to a PSS/PDDA multi-layer coating.

The thickness of the present film depends upon the arrangement of and types of elements that are used for its construction and normally ranges between about 20 μm and about 1,500 μm, or between about 30 μm and about 1000 μm, or between about 50 μm and about 800 μm. By way of example, in a film having a Ag/AgCl anode, an electrolytic gel of PEO/PVA-co-amine/BMIPF$_6$/Polycup® 172, and a cathode of TBBQ-modified carbon fibers, the thickness of the entire film was ~300 μm. Most of the film thickness comprised the electrolyte gel and the cathode since the Ag/AgCl layer has a thickness of only ~1-10 μm.

In another film having a carbon cloth anode, an electrolyte gel of PEO/PVA-co-amine/BMIPF$_6$/Polycup® 172, and a cathode of TBBQ-modified carbon cloth, the thickness of the film was ~800 to 1000 μm, while the thickness of the carbon cloth alone was ~400 to 500 μm.

The thickness of screen printed layers of the film range between 1 and 20 μm, and preferably between about 1 to about 10 μm.

After the present film is fabricated, the electrolye gel medium is permitted to accumulate oxygen and water, and electrode leads are connected between the electrodes and appropriate terminals of a source of an electrical potential, such as a battery. When a sufficient amount of oxygen and water have accumulated in the coating, it is ready for activation.

The present invention also includes a method of producing activated peroxides in an electroactive film. The novel method comprises providing an electroactive film comprising a first electrode that is spaced apart from a second electrode, a water insoluble electrically conductive medium which is permeable to moisture and oxygen and which contacts both electrodes, an electrocatalyst which can be reversibly oxidized and reduced and which facilitates the production of a peroxide when an electrical potential is imposed across the electrodes, and a peroxide-activating catalyst which converts the peroxide to an activated peroxide; and applying an electrical potential across the electrodes.

The present invention also includes a method of decontaminating a surface of a substrate that is susceptible to contamination with a contaminant. The method involves applying to the surface a film comprising a first electrode that is spaced apart from a second electrode, a water insoluble electrically conductive medium which is permeable to moisture and oxygen and which contacts both electrodes, an electrocatalyst which can be reversibly oxidized and reduced and which facilitates the production of a peroxide when an electrical potential is imposed across the electrodes, and a peroxide-activating catalyst which converts the peroxide to an activated peroxide; connecting the electroactive film to a source of an electrical potential; and when the surface is contaminated, applying an electrical potential to the electroactive film, thereby producing the decontaminating agent and destroying the contaminant.

The present method can further include the step of ceasing the application of an electrical potential to the electroactive film, thereby ceasing the production of the decontaminating agent. After the electrical potential is removed, the film can be exposed to air and oxygen is permitted to enter the coating from the air. Also, water vapor can be permitted to enter the coating. After oxygen and water are restored to the film the step of applying an electrical potential to the electroactive coating, thereby producing the decontaminating agent and destroying the contaminant can be repeated.

Articles that have been coated with a film of the present invention are also included within the scope of the invention.

The following examples describe preferred embodiments of the invention. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims which follow the examples. In the examples all percentages are given on a weight basis unless otherwise indicated.

General Procedures

Measurement of $H_2O_2$ in Polymer Electrolyte Gels:

A quantitative analytical approach using the Apollo 4000 Free Radical analyzer (World Precision Instruments) was developed to verify the presence of $H_2O_2$ generated in polymer gel electrolyte systems. Crosslinked and uncrosslinked PVA/PVA-co-Am/BMIPF$_6$ polymer gel electrolytes deposited onto carbon fiber electrodes were used in these studies. Since uncrosslinked electrolytes are soluble in water and are not stable under normal field conditions, the films were crosslinked using Polycup 172 crosslinker. The resulting crosslinked electrolytes were also studied and their $H_2O_2$ generation capability was also measured. Another important factor to consider in these electrolytes was their oxygen diffusion properties. Oxygen diffusion through uncrosslinked PVA/PVA-co-Am/BMIPF$_6$ polymer gel electrolytes was also determined.

A quantitative method to determine the concentration of $H_2O_2$ generated in the polymer gel electrolyte was developed using an Apollo 4000 Free Radical Analyzer from World Precision Instruments (WPI). The polymer gel electrolyte used in this experiment consisted of uncrosslinked and crosslinked polyvinyl alcohol (PVA)/Polyvinyl alcohol-co-amine (PVA-co-Am, medium molecular weight (M12) or low molecular weight (L12)/1-butyl-3-methylimidazolium hexafluorophosphate (BMIPF$_6$). The gel solution was deposited onto carbon fibers fixed on glass or polycarbonate substrates. For uncrosslinked films, the deposited gel solution was dried in air. To crosslink the PVA and PVA-co-Am binders, a crosslinker (Polycup 172) was added into the gel solution and thermally crosslinked at 100-120° C. for about 60 to 120 minutes. Another approach to form crosslinked films used 87-89% hydrolyzed PVA mixed with PVA-co-Am and BMIPF$_6$. The formed films were then thermally crosslinked by heating in vacuum at 70° C. for 30 min, followed by heating at 150° C. for another 30 min. The electrochemical properties of the crosslinked films containing various amounts of BMIPF$_6$ ionic liquid were studied using cyclic voltammetry. Good electrochemical properties were observed as evidenced by the measured currents comparable to that of the uncrosslinked films. BMIBF$_4$ could be substituted for BMIPF$_6$ in the above procedures.

To determine the concentration of $H_2O_2$ generated using the electrolytes above, constant potential (−0.7V) was applied across the electrodes for certain periods of time. After generation, the device was soaked in water to extract the $H_2O_2$ generated in the polymer gel electrolyte. The uncrosslinked films dissolved in water together with the $H_2O_2$ while the crosslinked films, which were insoluble in water, underwent minimal swelling and maintained their form. The devices were removed from the water solution and the water containing $H_2O_2$ extracted from the films was taken for analysis. Aliquots were injected in phosphate buffer solution (PBS) containing the Apollo analyzer probe. In this analysis, the presence of $H_2O_2$ was detected by a step change in current, which was proportional to the $H_2O_2$ concentration in solution. Results obtained from uncrosslinked samples showed step changes in current when aliquots of the water extract were added in the buffer solution. A similar device was made and used as a control. This control device was treated similarly as the sample except that it was not used to generate $H_2O_2$. Aliquots from the water extract obtained from the control were also injected to the phosphate buffer for $H_2O_2$ concentration analysis. Results obtained from the control sample did not show step changes in current signifying the absence of $H_2O_2$. The concentration of $H_2O_2$ obtained from the uncrosslinked films was 2.4 µM ($8.2 \times 10^{-6}$%) based on the calibration curve generated using $H_2O_2$ standard solutions. The same procedure was followed using crosslinked polymer gel electrolyte films. After electrochemical generation of $H_2O_2$, the device was soaked in water to extract the $H_2O_2$ generated in the film. Aliquots taken from the water extract indicated the presence of $H_2O_2$ at 3.1 µM ($1.1 \times 10^{-5}$%) concentration. The control device did not show presence of $H_2O_2$. Crosslinking the films improved their mechanical properties, water resistance, and they showed good adhesion when coated on glass. The crosslinking process also allowed repeated use of the films for $H_2O_2$ generation. Repeated electrochemical generation of $H_2O_2$ was performed using the same crosslinked electrolytes mentioned above. The concentrations obtained for the three runs were comparable and in the range of $3 \times 10^{-6}$%.

EXAMPLE 1

This example illustrates the formation of a carbon electrode on a substrate.

Screen Printing:.

Carbon layers that can serve as an electrode for the present films can be applied by screen printing of conductive carbon ink. Examples of suitable inks include XM-740 flexible carbon ink available from Conductive Compounds, Londonderry, N.H., or Electrodag® PF-407C carbon ink from Acheson Colloids Company, Port Huron, Mich.

The ink is screen printed either directly onto the surface of a substrate, or onto a pre-coating that has been applied to the substrate, or onto the surface of a cured gel layer. The ink is screen printed through a 196-mesh screen and then dried in a 100° C. oven for 10-30 minutes.

An electrode lead can then be attached to the carbon layer for connection to a source of electrical potential.

Carbon Cloth and Carbon Paper:

Carbon cloth "A" and "D" available from E-Tek Division, BASF Fuel Cell, Inc., Somerset, N.J., and carbon paper TGP-H-060 available from Toray Industries, Inc., Decatur, Ala. were also used as carbon electrodes. The cloth or paper was applied as a layer over a layer of electrically conductive gel and could then optionally be covered with another layer of the same gel. An electrode lead could be attached to the cloth or paper for connection to a source of electrical potential.

Carbon Powder:

Raven carbon black, available from Columbian Chemicals Company, Marietta, Ga., was dispersed in n-hexane and spray coated using an aerosol spray canister onto a surface to create a carbon layer electrode. An electrode lead could be applied to the layer for connection to a source of electrical potential.

EXAMPLE 2

This example illustrates the deposition of a quinone coating onto a carbon electrode to form a (non-covalently bound) coated electrode.

Ethanol Solution Method:

Carbon electrode material was contacted at room temperature with 10% Nitric acid for 2 to 4 hours, then washed with water, dried and contacted at room temperature with 1 M NaOH for another 2 to 4 hours, then washed with water and dried.

A solution was prepared that contained the desired quinone in ethanol. By way of example, although different concentrations of the quinone could be used, solutions of about 0.01 M-1 M, or about 0.01-0.05M quinone in ethanol, or from about 0.1% to about 10% by weight of the quinone, were found to be useful.

The treated carbon materials were placed in the quinone solution for about 6 to 12 hours, taken out, dried in air and then washed three times with Dl water, and immersed in Dl water for 12 hours, then taken out and dried. The carbon materials coated with quinone were then ready for use.

Acetonitrile Solution Method:

Carbon fibers were treated with acid as described above. A solution of tetrabromobenzoquinone (TBBQ) (0.05M) in acetonitrile was drop casted onto the treated fibers and dried. The fibers were then washed with 0.1M sulfuric acid and then with deionized water.

Electrodeposition:

Carbon fiber electrodes were used as substrates (Working Electrode-WE) in a 3-electrode configuration with RE: SCE and CE: C Fiber electrodes. The electrolytic solution consisted of 0.01M (10 mM) Anthraquinone Diazonium chloride (Fast red AL salt) and 0.1M Tetrabutyl Ammonium Tetrafluoroborate in Acetonitrile medium. Quinone was deposited on the carbon fiber by subjecting them to cyclic voltammetry (CV) between 0.65 to –0.45V vs. SCE using Gamry at 200 mV/s scan rate.

EXAMPLE 3

This example illustrates the electrochemical modification of carbon fiber electrodes by covalently-grafted anthraquinone Carbon fiber electrodes were used as substrates (working electrodes) in the 3-electrode configuration (Reference Electrode RE: SCE; Counter Electrode CE: Carbon Fiber Electrode). These electrodes are made as a bunch of 5 strands taped together at one end using Aluminum tape and immersed in solution to 3 cm depth at the other end (single strands are pulled out of a twill weave fabric obtained from Aerospace Composites, ACP Composites, Livermore, Calif.).

The electrolytic solution consists of 0.01M (10 mM) Anthraquinone Diazonium chloride (Fast red AL salt) and 0.1M Tetrabutyl Ammonium Tetrafluoroborate in Acetonitrile medium. Carbon Fiber electrodes were used as substrates (Working Electrode-WE) in a 3-electrode configuration with RE: SCE and CE: C Fiber electrodes. A schematic representation of the procedure is shown in FIG. 3.

Quinone was deposited on the carbon fiber by subjecting them to cyclic voltammetry (CV) between 0.65 to –0.45V vs SCE using Gamry at 200 mV/s scan rate. The covalent grafting process was then completed by applying constant potential (–0.2 V vs SCE for 20 min.) to the coated electrodes.

Cyclic voltammetry was performed between 0 to –1.25 V vs SCE in 0.1M KOH (pH 13), under $N_2$ bubbled condition for 3 cycles at different scan rates (10 mV/s, 20, 50, 100, 200 mV/s).

Stability of the covalently grafted quinone on carbon fiber electrode surface was studied by conducting a cyclic voltammetry experiment between 0 to –1.25V vs SCE at 200 mV/s scan rate in 0.1M KOH solution for a total of 300 cycles. This was conducted to verify the stability of the covalently bound quinone on carbon fiber surface. Results showed the initial removal of physically adsorbed quinone followed by covalently bound quinone remaining on the electrode even after the $100^{th}$ through the $300^{th}$ cycle. A parallel test with a carbon electrode having only physically adsorbed quinone showed that almost all of the quinone had been removed from the electrode by the $100^{th}$ cycle.

The covalent quinone modified carbon fiber electrodes are ready for use in generating $H_2O_2$ in a film of the invention. Typically, the cell set-up consists of covalent-quinone modified carbon fiber working electrode(s) separated from carbon fiber counter electrode(s) by a polymer gel electrolyte.

EXAMPLE 4

This example illustrates the formation of film of the present invention having a PVA/PVA-co-amine/$BMIPF_6$ electrically conductive gel.

Solid state films for generation of hydrogen peroxide were fabricated using carbon-based electrodes. Two-electrode devices comprising a $H_2O_2$-generating electrode (working electrode) and a counter electrode were fabricated. The electrodes were prepared either by screen printing commercially available carbon inks or by fixing commercially available carbon fibers onto a variety of flexible or rigid substrates including polycarbonate, glass, textiles, and fabric materials.

PVA and PVA-co-amine were separately dissolved in deionized water and combined to make 5% by wt. each of PVA and PVA-co-amine. Aliquots were taken from this solution and $BMIPF_6$ was added to make 1:1 ratio of $BMIPF_6$ with PVA-co-amine and PVA. The amount of $BMIPF_6$ could be varied to increase the ionic conductivity of the gel without compromising the film-forming properties. The liquid mixture was thoroughly mixed and deposited onto the two-electrode device and dried at room temperature to form a solid-state gel electrolyte. Once dried, the electrochemical properties of the device were determined by cyclic voltammetry and chronoamperometry.

Other polymeric systems, such as carboxymethyl cellulose (CMC) and polyethylene oxide (PEO) could be used in place of, or in addition to, the PVA to serve as binders for the $BMIPF_6$ in the electrolyte gel. Similarly, other ionic liquids could be used in place of the $BMIPF_6$.

Optionally, a crosslinking agent, such as Polycup 172, could be added to the gel-forming liquid and crosslinked by heat in order to strengthen the gel and make it more durable and less water soluble.

EXAMPLE 5

This example illustrates the formation of a film of the present invention comprising carbon electrodes and PEO/PVA-co-amine/BMIPF$_6$/Polycup 172 film as the conductive gel.

A solution of 2% PEO (M.W. 8,000,000, available from Sigma-Aldrich, St. Louis, Mo.)/1 % PVA-co-amine (PVA-co-amine) w/w was prepared in water by mixing at room temperature. The solution was heated to about 75° C. and constantly stirred until no polymer clumps were present (typically several days). Once fully dissolved, 10 ml of this solution was added with mixing to 300 µl of BMIPF$_6$ (98+%, available from Alfa-Aesar) along with 20 µl of Polycup® 172, available from Hercules, Inc., Wilmington, Del. The solution was then stirred vigorously to mix all the components. 200-300 µl of the liquid was then pipetted over the top of the carbon substrate (anode) and dried under ambient conditions. Another layer of the same volume was then added over the first one and dried. The cathode material, which could be carbon cloth, carbon fibers, carbon paper, or another layer of carbon ink, was then placed over the gel and more gel (200-300 µl) was deposited over the cathode material. The device was allowed to dry under ambient conditions and then was crosslinked in a 100° C. oven for 60 minutes.

The gel was typically used as the polymer electrolyte gel in films of the present invention and served to separate the electrodes and to provide electrical conductivity. Thus the gel layer had to be sufficiently thick to prevent shorting anode to cathode. The thickness of the gel layer between electrodes was typically about 50-400 µm, and usually about 300 µm.

EXAMPLE 6

This example illustrates methods for the immobilization of TAML® peroxide activating catalyst in the present film.

The solubility of TAML® catalyst in water posed a problem in its use under normal field conditions since the presence of water can easily leach it from the polymer electrolyte gel. It was preferred, therefore, that TAML® be immobilized onto a suitable matrix to allow formation of a stable polymer-TAML® catalyst on top of the polymer gel electrolyte. Using this configuration, the H$_2$O$_2$ generated in the polymer gel electrolyte can diffuse to the surface and react with the TAML® immobilized on its surface to create activated peroxide.

Two different routes of TAML® immobilization were investigated. In one route, a TAML® catalyst was immobilized on Dowex resin resulting in enhanced reaction rates when reacted with H$_2$O$_2$ in solution compared to reactions ran in the absence of the catalyst. The immobilization process produced a catalyst that was insoluble in water and other common aqueous and organic solvents and which prevented leaching under normal field conditions. In another approach, the same ion-exchange chemistry using poly(diallyldimethylammonium chloride) (PDDA) was used, where the negatively charged iron center exchanged with the chloride ion of PDDA. Enhanced bleaching rates were also observed when this immobilized TAML® was reacted with H$_2$O$_2$ both in solution and on the surface of the polymer gel electrolyte compared to when H$_2$O$_2$ was used by itself.

Ion-Exchange Resin Method:

A TAML® catalyst was immobilized in an ion exchange resin (Dowex® resin 1×2-200). The existing chloride ions in Dowex® were replaced with substituents anion groups of TAML®, resulting in immobilized-TAML® that was insoluble in common aqueous and organic solvents.

Dowex®, 1×2-200 (15 mg, available from Dow Chemical Co.) was placed in a beaker with 2 ml of deionized water. A solution of TAML® (10 mg) in 3 ml deionized water was added to the resin in the beaker. This was about twice the amount of TAML® theoretically required for total chloride replacement on the resin. The contents of the beaker were swirled (without mechanical agitation) for 5 minutes and allowed to sit at room temperature for 20 minutes to equilibrate. The swirling and sitting was repeated 4 times. The solution was decanted from the resin and the resin was washed with deionized water until the decantate was not colored.

The amount of TAML oanion immobilized in the resin (~20 mol %) was determined by titrating the supernatant obtained from the ion-exchange reaction with silver nitrate. The effectiveness of the immobilization process and the oxidizing ability of immobilized-TAML® when reacted with H$_2$O$_2$ were determined using phenol red dye as a sample substrate. The same concentration of H$_2$O$_2$ was added into solutions containing phenol red dye with and without TAML®. The solution containing insoluble immobilized-TAML® catalyst changed color (bleached) instantly upon addition of H$_2$O$_2$ while no color change was observed for the phenol red dye solution without TAML® catalyst. Tests showed ~42% decrease in absorbance of phenol red dye with immobilized-TAML® catalyst and ~6% decrease in absorbance without TAML® catalyst. Photographs also showed a distinct color change as soon as H$_2$O$_2$ was added into the mixture with TAML® while no color change was observed in the absence of TAML® catalyst.

A preliminary kinetic study was conducted on the bleaching of phenol red dye using H$_2$O$_2$ with and without immobilized-TAML®. The reaction was considered a pseudo first order approximation under the assumption that the much higher concentration of H$_2$O$_2$ used compared to the concentration of phenol red, would remain constant throughout the measurement period. Based on the equation: $\ln[A] = -k_1 t + \ln[A_0]$, where "A" is absorbance, the natural logarithms of the absorbances at 432 nm were plotted versus time "t" to obtain the rate constant $k_1$ (slope). The half-life was calculated using the equation $t_{1/2} = 0.693/k_1$. Results indicated that the presence of immobilized-TAML® resulted in a rate increase of 11-fold compared to H$_2$O$_2$ alone.

Layer-By-Layer Method:

The same ionic bonding chemistry discussed above was utilized in the TAML® immobilization process using poly (diallyldimethylammonium chloride) (PDDA). The chloride anion in PDDA was replaced by TAML® anion and the resulting solution was deposited on the surface of the gel electrolyte. The preferred process involved the formation of multi-layers (at least three sets were found to be preferred) on the surface of the polymer gel electrolyte consisting of a first layer of negatively charged poly(styrene sulfonate-sodium salt) (PSS-Na$^+$), followed by a layer of positively charged PDDA, and with this sequence repeated at least twice more to form three sets of double layers (See illustration in FIG. 7). TAML® was then immobilized on the topmost PDDA layer by dropping a solution of TAML® in deionized water (0.1 µM, pH around 7, room temperature) onto the topmost PDDA layer and permitting it to soak into the film for about 2-4 hours. The multi-layer approach provided ionic interactions between the negatively charged PSS layer and the positively charged PDDA layers resulting in stable layer formation. The range of the amount of TAML® applied per unit surface area of the film was about 0.01 to about 0.1 µg/cm².

Figure 9:
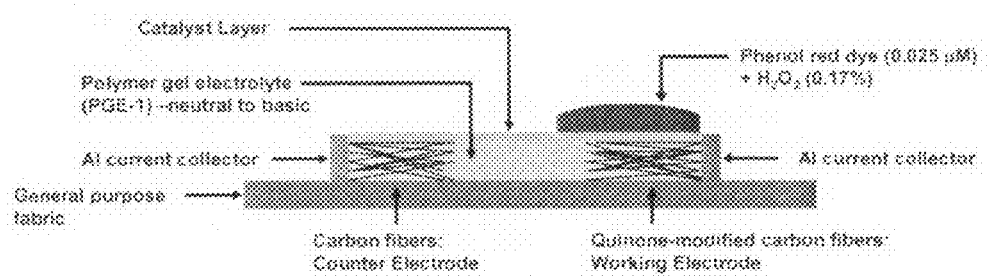
FIG. 9 is a schematic representation of the film device used for the phenol red bleaching test for activity of immobilized TAML in a PSS/PDDA-TAML multi-layer coating located on top of an electrolyte gel layer.

The stability and effectiveness of the ion exchange process and PDDA-TAML® deposition on the surface were tested by placing a mixture of phenol red dye and low concentration of $H_2O_2$ on the surface. After a minute, the phenol red dye bleached, indicating the presence of TAML® on the top layer of the coating system. This test was reproduced several times over a period of more than two weeks, which indicated effectiveness and stability of the PSS/PDDA-TAML® layer deposited on the surface. FIG. 9 shows a schematic diagram of the bleaching test on the surface of the coating system containing a layer of PSS/PDDA-TAML®.

The rate of bleaching for the film having the top layer of immobilized TAML® was much faster (up to 280 times faster) compared to the same test with phenol red dye solution was placed on the surface of the coating system without the PSS/PDDA-TAML layers. After bleaching the dye solution on the surface, the coating can be washed with water, dried in air or can be blotted/wiped with a Kimwipe prior to the next run. Performing this process repeatedly showed the stability and reusability of the integrated polymer coating. In fact, the activity of the immobilized TAML® was stable over 20-30 cycles.

EXAMPLE 7

This illustrates the generation of hydrogen peroxide in a film of the present invention to decontaminate the surface of the film.

$H_2O_2$ is generated from oxygen in air in an electrochemical process utilizing oxygen present in air and a quinone derivative as an electrocatalyst. The quinone derivative is electrochemically reduced to hydroquinone derivative by applying constant potential to a specially modified electrode containing the quinone. In the presence of oxygen in air or in solution, the hydroquinone derivative spontaneously oxidizes to form the original quinone and at the same time the oxygen reduces to form $H_2O_2$. The $H_2O_2$ generating electrode (working electrode) used in this system consists of carbon fibers coated with tetrabromo-p-benzoquinone monomer (TBBQ). The counter electrode used consists of unmodified carbon fibers. Up to 0.6% (176 mM) $H_2O_2$ can be electrochemically generated in solution and concentrations in the micromolar range (µM) was generated using crosslinked polymer gel electrolytes.

To generate $H_2O_2$ in the coating system, a polymer gel electrolyte consisting of polyethylene oxide (PEO), medium molecular weight polyvinyl alcohol-co-amine (PVA-co-Am, M12), 1-butyl-3-methylimidazolium hexafluorophosphate ionic liquid (BMIPF$_6$), and Polycup 172 crosslinker was formed as discussed above in Example 6. The gel was observed to be stable in water and has been stable enough to be used repeatedly for surface detoxification purposes.

Since the peroxide activating catalyst (TAML®) used in this example has a high solubility in water, which posed a problem under field conditions, two different routes of immobilizing this catalyst in a polymer matrix that render it insoluble in water were developed as discussed in Example 6. The immobilization procedure used in this example was the layer-by-layer technique comprising alternating layers of poly(diallyldimethylammonium chloride) (PDDA) and poly (styrene sulfonate, Na) (PSS-Na+). Since TAML® occurs as an anion containing an iron center (Fe−), an ion exchange technique was used to immobilize TAML® anion by exchanging it with the chloride ion in PDDA. The PDDA/PSS/PDDA-TAML® multi-layer was found to be stable in water and the effectiveness of TAML® immobilization and layer formation were tested by bleaching phenol red dye placed on its surface.

A film of the present invention was fabricated onto a general purpose fabric by fabricating a quinone-coated carbon electrode onto the fabric spaced apart from another carbon electrode, followed by a layer of the polymer gel electrolyte (PGE), and finally by the PDDA/PSS/PDDA-TAML® multilayer. Electrode leads were attached to each electrode. This device was used to electrochemically generate $H_2O_2$, which was activated in the presence of TAML® catalyst and caused surface detoxification of chemical and biological surrogate agents. The surface detoxification properties of the coating systems with and without TAML® catalysts and with and without $H_2O_2$ generation were conducted on chemical and biological surrogates. Results showed that the polymer gel electrolyte itself destroys *E. coli*, *S. aureus*, and *A. niger* completely and destroys *B. atrophaeus* to a certain extent (5.5-log kill). The effectiveness of the PGE in destroying *B. atrophaeus* increases to a 6-log kill when $H_2O_2$ was generated. In the presence of PSS/PDDA-TAML® (immobilized) on the surface, 4.5-log kill was obtained after 24-hour $H_2O_2$ generation compared to a 7-log kill when PSS/PDDA-TAML® was not present on the surface. It is believed that the absence of the PSS/PDDA-TAML® on the surface allows *B. atrophaeus* to be in direct contact with PVA-co-Amine component of the polymer gel electrolyte, which was found to destroy the spore's cell membrane resulting in more effective destruction when $H_2O_2$ is generated electrochemically. It is believed that the presence of PSS/PDDA-TAML® layer on the surface of the polymer gel electrolyte prevents *B. atrophaeus* from directly contacting the polymer gel electrolyte containing PVA-co-amine, thereby lengthening the time needed to destroy and penetrate the spore's cell membrane. Although significant log kill (4.5-log kill, target is 4 to 5-log kill) was achieved within 24 hours, it is believed that this can be improved by depositing a thin layer of PVA-co-amine on the surface of PSS/PDDA-TAML®, which should destroy the cell membrane and allow the electrochemically generated $H_2O_2$ to further destroy spores in shorter time periods.

Surface detoxification of demeton-s-methyl (DSM) using the integrated coating system showed oxidation to form its sulfoxide derivative (DSMSO) (favored product) after 4 hours of $H_2O_2$ generation in the presence of TAML® catalyst on the surface (PSS/PDDA-TAML®) without forming the sulfone derivative (DSMSO$_2$) (unfavored oxidation product).

The polymer coating system used in these experiments consisted of PEO, PVA-co-Am-M12, BMIPF6, and Polycup 172 with PSS/PDDA-TAML® immobilized on its surface. It was observed from the control experiments that DSM starting material (95%) contained DSMSO and in some cases, DSMSO$_2$ in small amounts, which can also be due to DSM oxidation when exposed to oxygen in air. On the control device (no $H_2O_2$ generation), the relative amount of DSMSO was found to be 5% with respect to the total DSM+DSMSO amount. After 4 hours of $H_2O_2$ generation on the sample device, the relative amount of DSMSO with respect to the total DSM+DSMSO amount increased to ~40%. The increase in the relative amount of DSMSO indicates oxidation of DSM on the surface of the polymer coating system due to the activated peroxide formed during $H_2O_2$ generation (reaction of generated $H_2O_2$ with TAML® immobilized on the surface).

When PSS/PDDA-TAML® was not present on the surface of the polymer gel electrolyte, oxidation was not observed within 4 hours of $H_2O_2$ generation. This could have been due to the lower currents (nA range) observed during $H_2O_2$ generation compared to the surface detoxification experiments previously performed with PSS/PDDA-TAML® present (μA range). Also, the oxidation process in the absence of PSS/PDDA-TAML® could be slower compared to when TAML® is present on the surface. Table 1 summarizes surface detoxification results of chemical and biological surrogates.

TABLE 1

Summary of surface detoxification results on self-detoxifying polymer coating systems.

| Surrogate | PGE-3 (no $H_2O_2$) | PGE-3 (in-situ gen.$H_2O_2$) | PGE-3 with PSS/PDDA-TAML® on surface (no $H_2O_2$) | PGE-3 with PSS/PDDA-TAML® on surface (in-situ gen. $H_2O_2$) |
|---|---|---|---|---|
| Demeton-s-methyl (DSM) | No reaction | No-reaction (4 hrs) | No reaction | Sulfoxide (DSMSO) (4 hr), no sulfone |
| B. atrophaeus | 5.5-log kill (4 hr) | 6.0-log kill (4 hr) | No difference with LB control (4 hr) | No difference with LB Control (4 hr) |
| | | 7.0-log kill (24 hr) | 2-log kill (24 hr) | 4.5-log kill (24 hr) |
| E. coli | Complete kill | Complete kill | To be determined (TBD) | TBD |
| S. aureus | Complete kill | Complete kill | TBD | TBD |
| A. niger | Complete kill | Complete kill | TBD | TBD |
| *Diisopropylfluorophosphate (DFP) | TBD | TBD | TBD | TBD |
| *Half-mustard (HD) | TBD | TBD | TBD | TBD |

*Note: Detoxification and identification of degradation/oxidation products for DFP and HD were conducted in solution. Complete hydrolysis of DFP was observed in the presence of low concentrations of $H_2O_2$ with small catalytic effect (TAML®). Exclusive formation of the HD-sulfoxide derivative was obtained when HD is reacted with $H_2O_2$-TAML®, incomplete conversion was found when $H_2O_2$ was used alone at the same time period.
PGE-3 is composed of PEO/PVA-co-amine M12/BMIPF$_6$/Polycup® 172 crosslinker, cured in an oven at 100°-120° C. for 2 hours.

Figure 10:
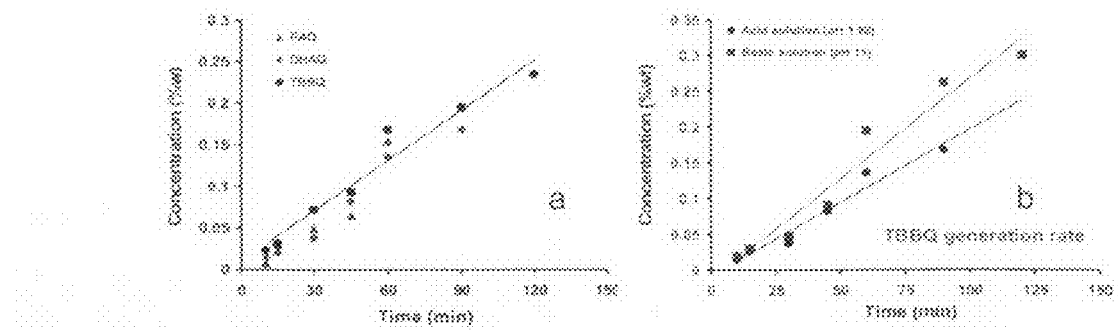
FIG. 10 shows graphs of the concentration of $H_2O_2$ versus time generated using (a) TBBQ, DHAQ and PAQ deposited onto carbon fiber electrodes under acidic (pH 1.62) conditions and (b) TBBQ deposited onto carbon fiber electrodes under basic (pH 11) and acidic (pH 1.62) conditions.

Films were fabricated as described above, but with carbon fiber electrodes onto which different quinones had been physically adsorbed. FIG. 10 shows the concentration of hydrogen peroxide generated as a function of time by devices having electrodes modified with TBBQ, DHAQ and PAQ. In FIG. 10(a) the pH was 1.62 and in FIG. 10(b), the pH was either 1.62 or 11, as indicated.

All references cited in this specification, including without limitation all papers, publications, patents, patent applications, presentations, texts, reports, manuscripts, brochures, books, internet postings, journal articles, periodicals, and the like, are hereby incorporated by reference into this specification in their entireties. The discussion of the references herein is intended merely to summarize the assertions made by their authors and no admission is made that any reference constitutes prior art. Applicants reserve the right to challenge the accuracy and pertinency of the cited references.

In view of the above, it will be seen that the several advantages of the invention are achieved and other advantageous results obtained.

As various changes could be made in the above methods and compositions by those of ordinary skill in the art without departing from the scope of the invention, it is intended that all matter contained in the above description and shown in the accompanying drawings shall be interpreted as illustrative and not in a limiting sense. In addition it should be understood that aspects of the various embodiments may be interchanged both in whole or in part.

What is claimed is:

1. In an electroactivated film that includes a first electrode that is spaced apart from a second electrode, a water insoluble electrically conductive medium which is permeable to moisture and oxygen and which contacts both electrodes, an electrocatalyst which can be reversibly oxidized and reduced and which facilitates the production of a peroxide when an electrical potential is imposed across the electrodes, and optionally a peroxide-activating catalyst which converts the peroxide to an activated peroxide;

the improvement wherein the water insoluble electrically conductive medium which is permeable to moisture and oxygen comprises a water insoluble polymer gel containing an ionic liquid, a polyvinyl alcohol/amine copolymer, a polymer selected from the group consisting of carboxymethyl cellulose, polyvinyl alcohol, and polyethylene oxide, and a crosslinking agent.

2. The improvement according to claim 1, wherein the polyvinyl alcohol/amine copolymer is one having the structure:

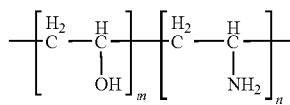

where the value of m plus n ranges from about 1,000 to about 100,000; and where the ratio of m and n is from about 99 to 1 to about 1 to 99.

3. The improvement according to claim 1, wherein the polyvinyl alcohol/amine copolymer is one having the structure:

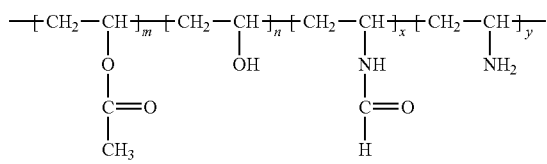

where:
m is 0-15 mole %
n is 50-99 mole %
x is 0-30 mole %, preferably 0.5-10 mole %, and
y is 0.2-50 mole %, preferably 1-25 mole %.

4. The improvement according to claim 3, wherein the value of m plus n ranges from about 1,000 to about 4,000.

5. The improvement according to claim 1, wherein the ionic liquid is selected from the group consisting of ethylammonium nitrate, mixtures of 1,3-dialkylimidazolium or 1-alkylpyridinium halides and trihalogenoaluminates, salts of hexafluorophosphate, salts of tetrafluoroborate, salts of bistriflimide, 1-ethyl-3-methyl imidazolium bis(trifluoromethanesulfonyl) amide, 1-butyl-3-methylimidazolium nitrate, 1-butyl -3-methylimidazolium tetrafluoroborate, 1-butyl-3-methylimidazolium chloride, 1-butyl-3-methylimidazolium hexafluorophosphate, protonated betaine bis(trifluoromethanesulfonyl)imide, N-butyl-N-methyl pyrrolidinium bis(trifluoromethanesulfonyl)imide, ammonium and halide salts of 1-alkyl-3-methylimidazolium, ammonium and halide salts of 1-alkylpyridinium, ammonium and halide salts of N-methyl-N-alkylpyrrolidinium, formate salts, alkylsulfate salts, alkylphosphate salts, glycolate salts, 1-alkylimidazole, and mixtures thereof.

6. The improvement according to claim 1, wherein the ionic liquid comprises 1-butyl-3-methylimidazolium hexafluorophosphate or 1-butyl-3-methylimidazoliumtetrafluoroborate.

7. The improvement according to claim 1, wherein the water insoluble polymer gel comprises polyvinyl alcohol/amine copolymer and polyvinyl alcohol crosslinked with a polyamide/epichlorohydrin crosslinking agent.

8. The improvement according to claim 1, wherein the water insoluble polymer gel comprises polyvinyl alcohol/amine copolymer and polyethylene oxide crosslinked with a polyamide/epichlorohydrin crosslinking agent.

9. The improvement according to claim 1, wherein the water insoluble polymer gel comprises about 0.1% to about 10% by weight of polyvinyl alcohol/amine copolymer, about 0.2% to about 20% by weight polyethylene oxide, about 0.2% to about 40% by volume of the ionic liquid, and 0.02% to about 2% by weight polyamide/epichlorohydrin crosslinking agent.

10. The improvement according to claim 1, wherein the water insoluble polymer gel comprises about 1% by weight of polyvinyl alcohol/amine copolymer, about 2% by weight polyethylene oxide, about 2% to about 20% by volume of the ionic liquid, and 0.02% to 2% by weight polyamide/epichlorohydrin crosslinking agent.

11. In a method of producing an electroactivated film suitable for surface decontamination that includes a first electrode that is spaced apart from a second electrode, a water insoluble electrically conductive medium which is permeable to moisture and oxygen and which contacts both electrodes, an electrocatalyst which can be reversibly oxidized and reduced and which facilitates the production of a peroxide when an electrical potential is imposed across the electrodes, and optionally a peroxide-activating catalyst which converts the peroxide to an activated peroxide;

the improvement comprising forming the water insoluble electrically conductive medium which is permeable to moisture and oxygen by crosslinking a polyvinyl alcohol/amine copolymer with a polymer selected from carboxymethyl cellulose, polyvinyl alcohol and polyethylene oxide in the presence of an ionic liquid to form a polymer electrolyte gel, wherein the electroactive film is fabricated onto a surface of a substrate.

12. The improvement according to claim 11, wherein the polymer electrolyte gel is crosslinked by heating.

13. The improvement according to claim 12, wherein the polymer electrolyte gel is crosslinked after being placed in contact with the first electrode.

14. The improvement according to claim 11, wherein the polyvinyl alcohol/amine copolymer is one having the structure:

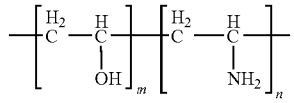

where the value of m plus n ranges from about 1,000 to about 100,000; and where the ratio of m and n is from about 99 to 1 to about 1 to 99.

15. The improvement according to claim 11, wherein the polyvinyl alcohol/amine copolymer is one having the structure:

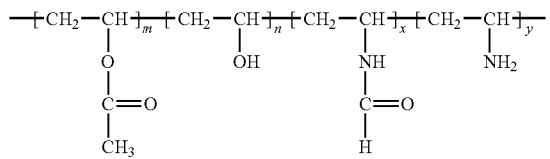

where:
m is 0-15 mole %
n is 50-99 mole %
x is 0-30 mole %, preferably 0.5-10 mole %, and
y is 0.2-50 mole %, preferably 1-25 mole %.

16. The improvement according to claim 11, wherein the ionic liquid comprises 1-butyl-3-methylimidazolium hexafluorophosphate or 1-butyl1-3-methylimidazoliumtetrafluoroborate.

* * * * *